(12) United States Patent
Jaeger et al.

(10) Patent No.: US 11,525,154 B2
(45) Date of Patent: Dec. 13, 2022

(54) DEVICES, METHODS, KITS, AND SYSTEMS FOR DETECTING MICROORGANISM STRAINS OR TARGET CELLULAR ANALYTES IN A FLUID SAMPLE

(71) Applicant: 3M INNOVATIVE PROPERTIES COMPANY, St. Paul, MN (US)

(72) Inventors: Jobst T. Jaeger, Kaarst (DE); Jeffrey D. Smith, Marine on St. Croix, MN (US); Waleri Wischnepolski, Neuss (DE); Henning Reuter, Willich (DE); Giuseppe M. Bommarito, Stillwater, MN (US); Manjiri T. Kshirsagar, Woodbury, MN (US); Scott D. Lehman, Marietta, GA (US); Edward I. Stamm, Jr., Roswell, GA (US); Guenter M. Zilligen, Grevenbroich (DE)

(73) Assignee: 3M Innovative Properties Company, St. Paul, MN (US)

( * ) Notice: Subject to any disclaimer, the term of this patent is extended or adjusted under 35 U.S.C. 154(b) by 500 days.

(21) Appl. No.: 15/559,117

(22) PCT Filed: Mar. 18, 2016

(86) PCT No.: PCT/US2016/023020
§ 371 (c)(1),
(2) Date: Sep. 18, 2017

(87) PCT Pub. No.: WO2016/149571
PCT Pub. Date: Sep. 22, 2016

(65) Prior Publication Data
US 2018/0051312 A1 Feb. 22, 2018

Related U.S. Application Data

(60) Provisional application No. 62/309,668, filed on Mar. 17, 2016, provisional application No. 62/135,425, filed on Mar. 19, 2015.

(51) Int. Cl.
*B01L 3/02* (2006.01)
*B01L 3/00* (2006.01)
(Continued)

(52) U.S. Cl.
CPC .............. *C12Q 1/22* (2013.01); *B01L 3/0275* (2013.01); *B01L 3/5029* (2013.01); *C12Q 1/04* (2013.01);
(Continued)

(58) Field of Classification Search
CPC ....... B01L 2200/028; B01L 2200/0684; B01L 2300/0681; B01L 2300/123;
(Continued)

(56) References Cited

U.S. PATENT DOCUMENTS

| 4,118,531 A | 10/1978 | Hauser |
| 4,729,846 A | 3/1988 | Matsui |

(Continued)

FOREIGN PATENT DOCUMENTS

| CA | 2612854 | 6/2008 |
| CN | 1369003 | 9/2002 |

(Continued)

OTHER PUBLICATIONS

International Search Report for PCT International Application No. PCT/US2016/023020, dated Sep. 13, 2016, 4 pages.

*Primary Examiner* — Lydia Edwards
(74) *Attorney, Agent, or Firm* — Adrian L. Pishko

(57) ABSTRACT

Devices for detecting microorganism strains or target cellular analytes are provided. The device includes a filter holder, the filter holder comprising a tip portion; a nonwoven article disposed on the tip portion of the filter holder; and an adaptor attacked to the filter holder, the adaptor defining an aperture. Methods of detecting microorganisms and/or cellular analytes in a fluid sample using the devices are also
(Continued)

provided. The method includes obtaining the device; placing a lumened or cannulated device in fluid communication with the device; and passing a fluid sample suspected of containing at least one microorganism strain or target cellular analyte from the lumened or cannulated device through the device and contacting the nonwoven article. The method further includes contacting the nonwoven article with at least one detection reagent and detecting the presence of the at least one microorganism strain or target cellular analyte concentrated by the nonwoven article. Kits and systems including the devices are also provided.

11 Claims, 8 Drawing Sheets

(51) Int. Cl.
    *B01L 99/00*           (2010.01)
    *C12Q 1/22*           (2006.01)
    *C12Q 1/04*           (2006.01)
    *G01N 33/543*       (2006.01)

(52) U.S. Cl.
    CPC .. *G01N 33/54386* (2013.01); *B01L 2200/028* (2013.01); *B01L 2200/0684* (2013.01); *B01L 2300/0681* (2013.01); *B01L 2300/123* (2013.01); *B01L 2400/0478* (2013.01); *B01L 2400/0605* (2013.01)

(58) Field of Classification Search
    CPC ..... B01L 2400/0478; B01L 2400/0605; B01L 3/0275; B01L 3/5029; C12Q 1/04; C12Q 1/22; G01N 33/54386
    See application file for complete search history.

(56) References Cited

U.S. PATENT DOCUMENTS

| | | | |
|---|---|---|---|
| 5,147,314 A * | 9/1992 | Vaillancourt | A61M 25/0111 604/158 |
| 5,597,645 A | 1/1997 | Pike | |
| 5,624,810 A | 4/1997 | Miller | |
| 5,807,312 A * | 9/1998 | Dzwonkiewicz | A61M 5/1424 604/248 |
| 6,045,913 A | 4/2000 | Castle | |
| 6,451,260 B1 | 9/2002 | Duesterhoeft | |
| 7,335,337 B1 * | 2/2008 | Smith | B01L 3/0275 422/513 |
| 7,422,868 B2 | 9/2008 | Fan | |
| 7,601,546 B2 | 10/2009 | Bayloff | |
| 8,039,206 B1 | 10/2011 | Keenan | |
| 8,609,330 B2 | 12/2013 | Rajagopal | |
| 10,774,300 B2 | 9/2020 | Hyman | |
| 2003/0012688 A1 | 1/2003 | Kippenhan, Jr. | |
| 2005/0250169 A1 | 11/2005 | Gonzalez | |
| 2006/0269445 A1 | 11/2006 | Basile | |
| 2008/0299600 A1 | 12/2008 | Bommarito | |
| 2009/0012425 A1 | 1/2009 | Mach | |
| 2012/0009588 A1 * | 1/2012 | Rajagopal | B01L 3/5082 435/6.15 |
| 2012/0073614 A1 | 3/2012 | Otani | |
| 2012/0156716 A1 | 6/2012 | Walsh | |

FOREIGN PATENT DOCUMENTS

| | | |
|---|---|---|
| CN | 1730664 | 2/2006 |
| CN | 1921803 | 2/2007 |
| CN | 101238206 | 8/2008 |
| CN | 101278195 | 10/2008 |
| CN | 201894877 | 7/2011 |
| CN | 103370133 | 10/2013 |
| CN | 103415617 | 11/2013 |
| CN | 103813845 | 5/2014 |
| CN | 104195036 | 12/2014 |
| FR | 2 672 995 | 8/1992 |
| GB | 2500866 | 10/2013 |
| JP | 2000-333668 | 12/2000 |
| JP | 2008-173399 | 7/2008 |
| WO | WO 98/08594 | 3/1998 |
| WO | WO 2008-137095 | 11/2008 |
| WO | WO 2009-046183 | 4/2009 |
| WO | WO 2009-046191 | 4/2009 |
| WO | WO 2009-085357 | 7/2009 |
| WO | WO 2010-078399 | 7/2010 |
| WO | WO 2010-078404 | 7/2010 |
| WO | WO 2010-114727 | 10/2010 |
| WO | WO 2012-061213 | 5/2012 |
| WO | WO 2012-078374 | 6/2012 |
| WO | WO 2012-078426 | 6/2012 |
| WO | WO 2012/122088 | 9/2012 |
| WO | WO 2013-184186 | 12/2013 |
| WO | WO 2013-184373 | 12/2013 |
| WO | WO 2014-151117 | 9/2014 |
| WO | WO 2015-047464 | 4/2015 |
| WO | WO 2015-094938 | 6/2015 |
| WO | WO 2016-149233 | 9/2016 |
| WO | WO 2016-149235 | 9/2016 |
| WO | WO 2016-149472 | 9/2016 |

* cited by examiner

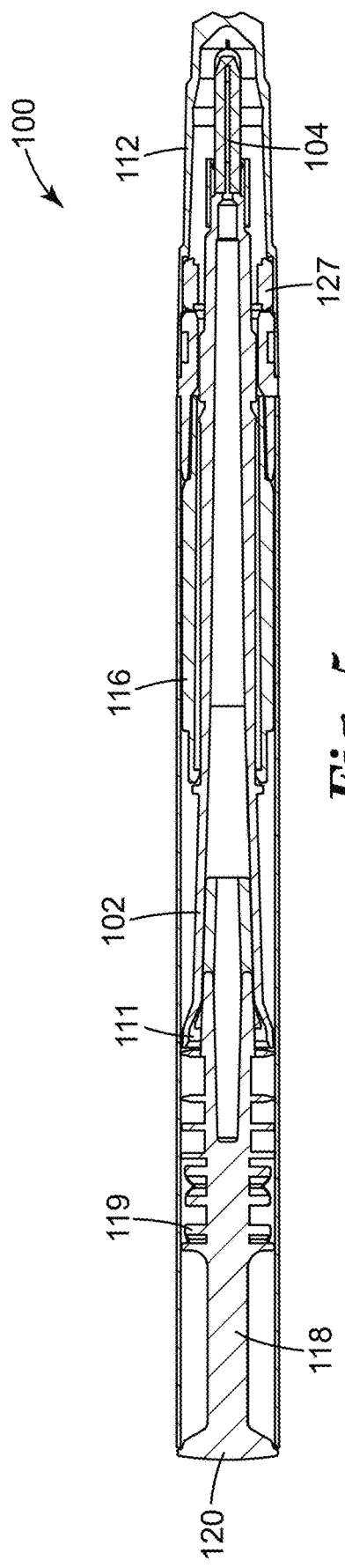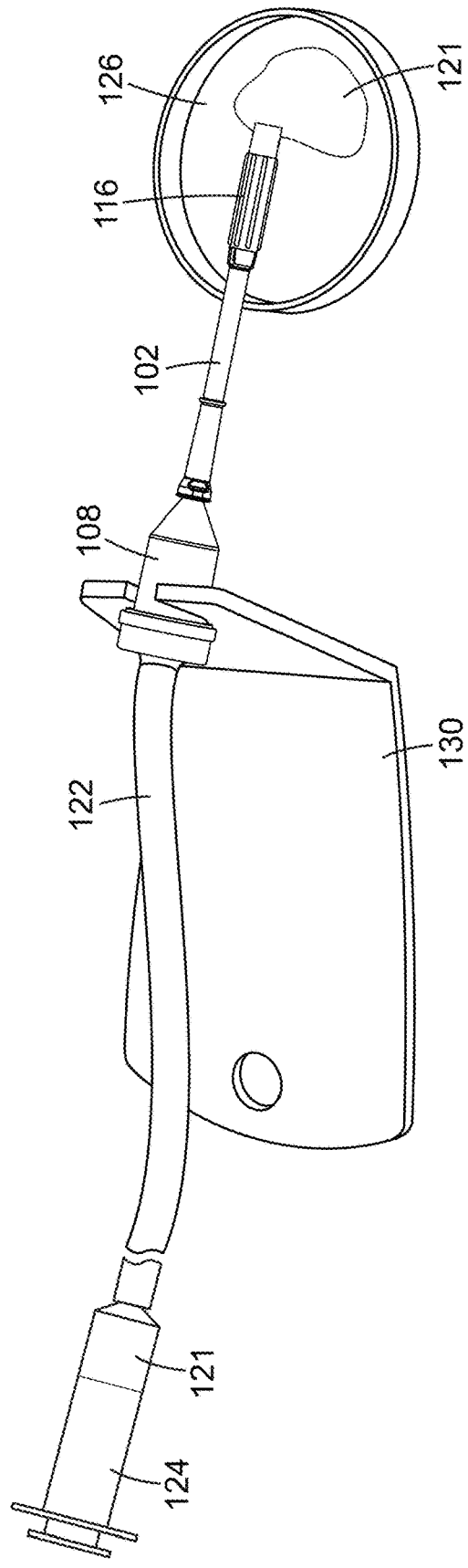
Fig. 5
Fig. 6

DEVICES, METHODS, KITS, AND SYSTEMS FOR DETECTING MICROORGANISM STRAINS OR TARGET CELLULAR ANALYTES IN A FLUID SAMPLE

CROSS REFERENCE TO RELATED APPLICATIONS

This application is a national stage filing under 35 U.S.C. 371 of PCT/US2016/023020, filed Mar. 18, 2016, which claims the benefit of U.S. application Ser. No. 62/135,425, filed Mar. 19, 2015, and U.S. application Ser. No. 62/309,668, filed Mar. 17, 2016, the disclosures of which are incorporated by reference in their entirety herein.

FIELD

The present disclosure relates to detecting microorganism strains or target cellular analytes in a fluid sample, such as using devices, kits, or systems.

BACKGROUND

It is often desirable or necessary to assay for the presence of bacteria or other microorganisms in various clinical samples, in order to determine the identity and/or the quantity of the microorganisms present. Bacterial DNA or bacterial RNA, for example, can be assayed to assess the presence or absence of a particular bacterial species even in the presence of other bacterial species. The ability to detect the presence of a particular bacterium, however, depends, at least in part, on the concentration of the bacterium in the sample being analyzed. Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or nonmagnetic particles). Such methods, however, have tended to be expensive and still somewhat slower than desired for at least some diagnostic applications. Non-specific concentration or capture of microorganisms has been achieved through methods based upon carbohydrate and lectin protein interactions. Various inorganic materials (for example, hydroxyapatite and metal hydroxides) have also been used to non-specifically bind and concentrate bacteria. Such non-specific concentration methods have varied in speed, cost, sample requirements, space requirements, ease of use, suitability for on-site use, and/or effectiveness.

Bacteria can cause problems in clinical applications, such as reprocessing of medical devices. Rapid detection methods based on ATP bioluminescence assays have been used to determine microbial contamination in fluids such as water, as they provide immediate results; however, the methods are limited by detection sensitivity because they require at least $1 \times 10^5$ colony forming units (cfu)/ml to elicit detectable responses. Interference from treatment chemicals can affect the bioluminescence, leading to erroneous results. One can increase the sensitivity of the ATP bioluminescence assay by using a larger volume of sample (e.g., 100 ml), but such methods can be difficult to implement in clinical settings.

SUMMARY

Devices, kits, and systems are provided that can be used to detect microorganisms and/or cellular analytes in fluid samples, such as water or aqueous dispersions.

In a first aspect, a device is provided. The device includes a filter holder, the filter holder comprising a tip portion; a nonwoven article disposed on the tip portion of the filter holder; and an adaptor attached to the filter holder, the adaptor defining an aperture.

In a second aspect, a method of detecting microorganisms and/or cellular analytes in a fluid sample is provided. The method includes obtaining a device (e.g., a device according to the first aspect); placing a lumened or cannulated device in fluid communication with the device; and passing a fluid sample suspected of containing at least one microorganism strain or target cellular analyte from the lumened or cannulated device through the device and contacting the nonwoven article. The method further includes contacting the nonwoven article with at least one detection reagent and detecting the presence of the at least one microorganism strain or target cellular analyte concentrated by the nonwoven article.

In a third aspect, a kit is provided. The kit includes a device (e.g., a device according to the first aspect); a cuvette containing at least one detection reagent; and a handle configured to be inserted into the filter holder.

In a fourth aspect, a system is provided. The system includes a device (e.g., a device according to the first aspect); a cuvette containing at least one detection reagent; a handle configured to be inserted into the filter holder; and a luminometer.

In a fifth aspect, another method is provided. The method comprises obtaining a device comprising a Y-shaped configuration; placing a lumened or cannulated device in fluid communication with the device; and passing a fluid sample suspected of containing at least one microorganism strain or target cellular analyte from the lumened or cannulated device through the device and contacting the nonwoven article. The method further comprises contacting the nonwoven article with at least one detection reagent and detecting the presence of the at least one microorganism strain or target cellular analyte concentrated by the nonwoven article. The device comprises 1) a filter holder, the filter holder comprising a tip portion; 2) a nonwoven article disposed on the tip portion of the filter holder; 3) a container configured to hold the filter holder; and 4) an adaptor attached to the container in a Y-shaped configuration, the adaptor defining an aperture.

In a sixth aspect, another kit is provided. The kit comprises a device comprising a Y-shaped configuration (e.g., a device according to the fifth aspect) and a cuvette containing at least one detection reagent.

In a seventh aspect, another system is provided. The system comprises a device comprising a Y-shaped configuration (e.g., a device according to the fifth aspect); a cuvette containing at least one detection reagent; and a luminometer.

BRIEF DESCRIPTION OF THE DRAWINGS

FIG. 5 is a schematic cross-sectional view of yet another exemplary device.

FIG. 6 is a schematic perspective view of an exemplary kit.

DETAILED DESCRIPTION

Figure 1A:
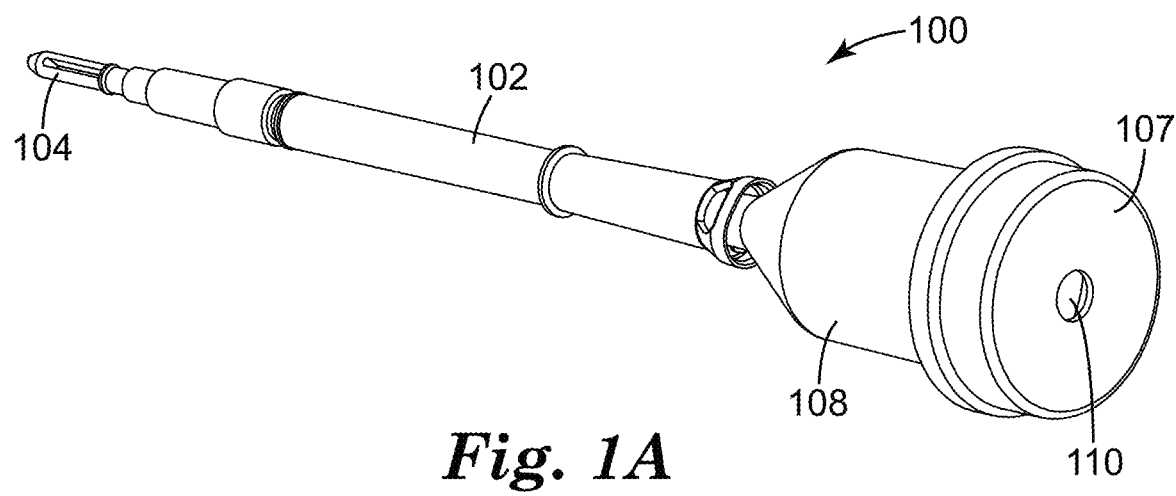
FIG. 1A is schematic perspective view of an exemplary device.

Devices, kits, and systems for monitoring of microbial quality of fluid samples are provided. The method combines a lumened or cannulated device in fluid communication with a device containing a nonwoven article that concentrates at least one microorganism or target cellular analyte, and detection of the microorganism or target cellular analyte. The nonwoven articles may be contacted with large volumes of fluid samples to concentrate the microorganism and/or target cellular analyte. Methods according to the disclosure are capable of readily detecting bacterial contamination in fluid samples in about 15 minutes. Accordingly, the nonwoven articles and methods can be suitable for clinical detection of microorganisms and target cellular analytes in fluid samples contacting a lumened or cannulated device.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example "A and/or B" means only A, only B, or both A and B.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The term "comprises" and variations thereof do not have a limiting meaning where these terms appear in the description and claims.

The term "consists essentially of" does not exclude the presence of additional materials which do not significantly affect the desired characteristics of a given composition or product. The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The term "cannulated device" means a device that includes a tube, such as a narrow flexible tube.

The term "cellular analyte" means an analyte of cellular origin (that is, a microorganism or a component thereof (for example, a cell or a cellular component such as deoxyribonucleic acid (DNA) or ribonucleic acid (RNA), proteins, nucleotides such as adenosine triphosphate (ATP), and the like, and combinations thereof); references to a microorganism or microorganism strain throughout this specification are meant to apply more generally to any cellular analyte).

The term "concentration agent" means a material or composition that binds microorganisms and/or cellular analytes from a fluid sample (preferably, having a cellular analyte capture or binding efficiency of at least about 60 percent, or at least about 70 percent, or at least about 80 percent, or at least about 90 percent), thereby concentrating the microorganisms and/or cellular analytes into a smaller volume than when present in the fluid sample.

The term "detection" means the identification of a cellular analyte (for example, at least a component of a target microorganism, which thereby determines that the target microorganism is present).

The term "endoscopy" means a procedure in which a medical device (e.g., a scope) is introduced into a body to give a view of one or more internal parts of the body.

The term "enmeshed" (in regard to particles in a fibrous porous matrix) means that the particles are entrapped in and on the fibrous porous matrix (and, preferably, distributed within it), rather than solely being borne on its surface.

The term "fibrillated" (in regard to fibers or fibrous material) means treated (for example, by beating) in a manner that forms fibrils or branches attached to a fiber's main trunk.

The term "fibrous porous matrix" means a nonwoven web or medium, (i.e., not a woven or knitted fabric), comprising interlaid fibers, for example, a web comprising fibers that are interlaid by meltblowing, spunbonding, or other air laying techniques; carding; wet laying; or the like.

Typically, the fibers have lengths of less than 100 millimeters and are uncrimped.

The term "fluid" means liquid, solution, or dispersion of solid or liquid in liquid.

The term "lumened device" means a device that includes a tubular interior or exterior shape.

The term "microorganism" means any cell or particle having genetic material suitable for analysis or detection (including, for example, bacteria, yeasts, viruses, and bacterial endospores).

The term "microorganism strain" means a particular type of microorganism that is distinguishable through a detection method (for example, microorganisms of different genera, of different species within a genera, or of different isolates within a species).

The terms "polymer" and "polymeric material" are used interchangeably and refer to materials formed by reacting one or more monomers.

The term "sample" means a substance or material that is collected (for example, to be analyzed).

The term "sample matrix" means the components of a sample other than microorganisms and/or cellular analytes.

The term "target cellular analyte" means any cellular analyte that is desired to be detected.

The term "target microorganism" means any microorganism that is desired to be detected.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in some embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Endoscopy procedures are performed using complex, reusable, flexible instruments that, when inserted into the body, may become heavily contaminated with patient biomaterial and microorganisms, including potential pathogens. Careful reprocessing of flexible endoscopes between patients is critical to reducing the risk of cross-contamination and the possible transmission of pathogens. Cleaning for these devices is typically defined as the removal of soil (e.g., organic and inorganic material) from objects and surfaces and it is accomplished manually or mechanically using water with detergents or enzymatic products. Failure to perform proper cleaning leaves behind organic and inorganic residues that may interfere with the disinfection process increasing the risk for reprocessing failures and patient infection. Thus, the need to evaluate the efficacy of cleaning and disinfection has been recognized as an important part of flexible endoscope reprocessing. A visually based method of verification, however, has severe limitations when applied to flexible endoscopes because the complex, narrow lumens in these devices cannot be directly visually inspected. Use of devices, methods, kits, and systems according to the present disclosure, which may be performed in real time, to test a rinsate from instruments following cleaning provides an opportunity to take any corrective action required such as re-cleaning and reprocessing. It has been discovered that it is possible to test a fluid sample suspected of containing at least one microorganism strain or a target cellular analyte directly from a medical instrument using the devices, methods, kits, and systems of the present disclosure. An advantage of direct testing is decreasing the opportunities for contamination of the fluid sample as compared to testing in which the fluid sample is undergoes additional handling steps.

Devices

Figure 1B:
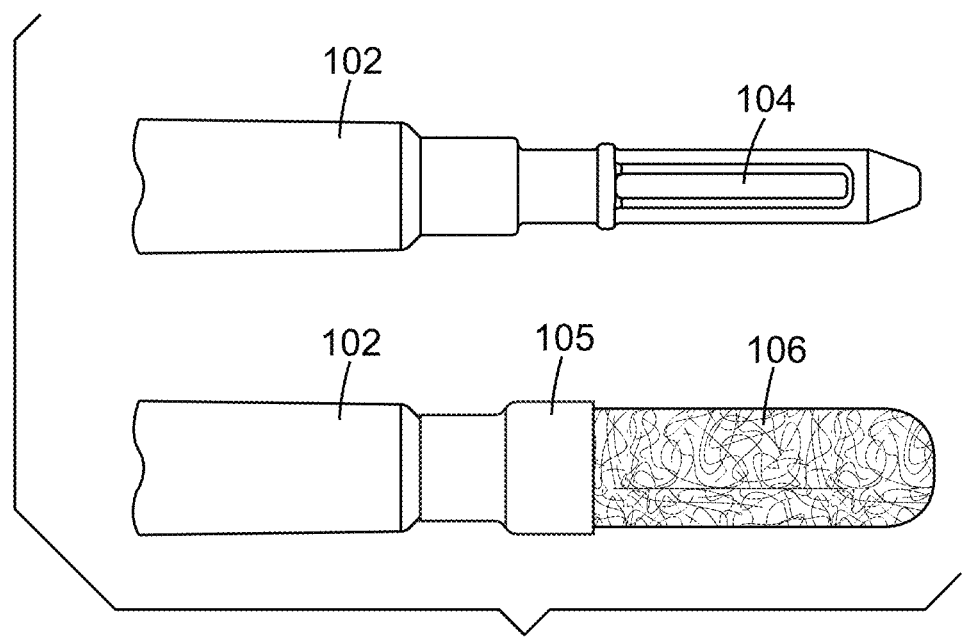
FIG. 1B is a schematic side view of an exemplary tip portion of a filter holder and a nonwoven article on a tip portion.

In a first aspect, a device is provided. The device includes a filter holder, the filter holder comprising a tip portion; a nonwoven article disposed on the tip portion of the filter holder; and an adaptor attached to the filter holder, the adaptor defining an aperture. Referring to FIGS. 1A and 1B, a device 100 includes a filter holder 102, the filter holder 102 comprising a tip portion 104; a nonwoven article 106 disposed on the tip portion 104 of the filter holder 102; and an adaptor 108 (removably) attached to the filter holder 102, the adaptor 108 defining an aperture 110. The nonwoven article is described in detail below.

In certain embodiments, the filter holder 102 and the adaptor 108 are integrally formed, while in other embodiments the filter holder 102 and the adaptor 108 are detachable. Integrally forming the filter holder 102 and the adaptor 108 potentially results in greater simplicity in manufacturing of the device 100, while providing a filter holder 102 that is a separate piece from the adaptor 108 allows for greater flexibility in employing the device 100, such as having the two pieces attached during certain steps and detached during other steps.

Each of the filter holder 102 and the adaptor 108 is optionally fabricated at least in part from a relatively rigid material (e.g., nylon, polysulfone, polycarbonate, or combinations thereof), or it may be formed using a more compliant polymer, such as silicone. Example materials for filter holder 102 and the adaptor 108 include, but are not limited to, any thermoplastic materials suitable for casting, profile extrusion, molding (e.g., injection molding) or embossing including, for example, polyolefins, polyesters, polyamides, poly(vinyl chloride), polymethyl methacrylate, polycarbonate, nylon, and the like.

In any embodiment, the adaptor 108 optionally comprises an elastomeric portion 107 that defines the aperture 110. Employing an elastomeric material for at least a portion of the adaptor that defines the aperture may provide the option of using an adaptor having an aperture of a single size for various lumened or cannulated devices of differing widths, due to the stretchability of the elastomeric material. In addition, elastomeric materials may assist in forming a pressure-tight seal between the adaptor and a lumened or cannulated device disposed through the aperture. Suitable elastomeric materials include for instance and without limitation, silicones, polyolefin elastomers, styrenic block copolymers, natural rubbers, and polyurethanes. Alternatively, the adaptor portion that defines the aperture may be formed of a more rigid material sized to fit a particular lumened or cannulated device, and/or include a resilient gasket 109 (see, e.g., FIG. 2) configured to form a pressure-tight seal between the adaptor 108 and a lumened or cannulated device disposed through the aperture.

As shown in FIG. 1A, in some embodiments the filter holder 102 and the adaptor 108 are attached in series (e.g. an end of the filter holder 102 is attached to an end of the adaptor 108). In such embodiments the nonwoven article 106 is typically disposed on the tip portion 104 distal from the adaptor 108. Referring to FIG. 1B, in many embodiments the nonwoven article 106 is configured to have a tube shape. Optionally, the nonwoven article 106 is secured to the tip portion 104 of the filter holder 102 using a resilient member 105 (e.g., an o-ring or collar) disposed around at least a portion of an exterior surface of the nonwoven article 106. When the nonwoven article 106 has a tube shape it may allow for tangential flow of a fluid sample that contacts the nonwoven article 106 while flowing through the device 100. An advantage of using tangential flow is that a volume of fluid sample will typically contact at least one major surface of the nonwoven article 106 for a greater amount of time than when the same volume of fluid sample passes from one major surface of the nonwoven article 106 through the opposing major surface of the nonwoven article. A greater contact time may result in greater capture of any microorganism strains and/or target cellular analytes by the nonwoven article.

Figure 2:
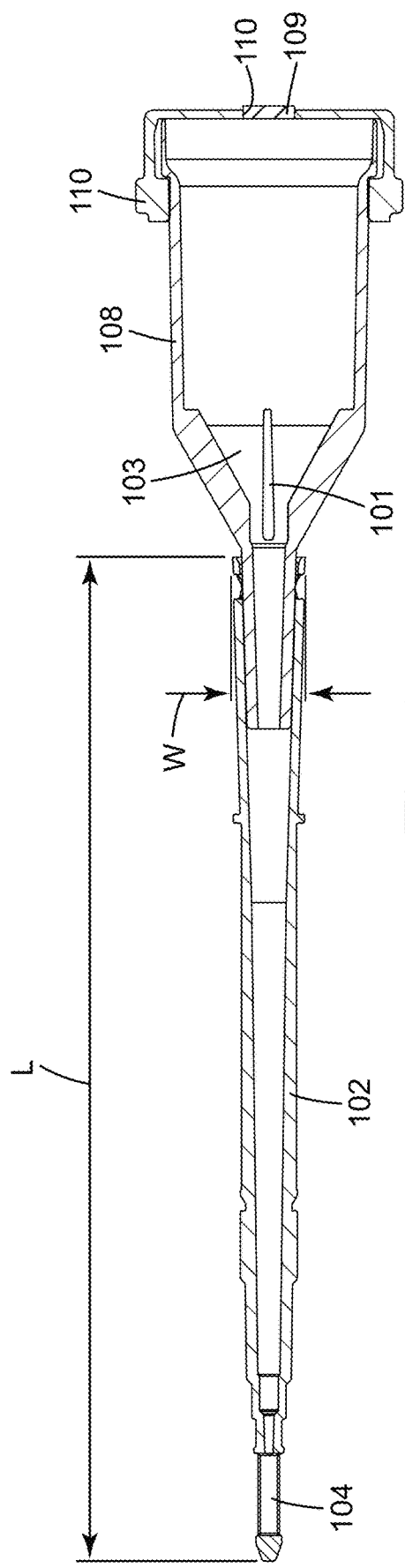
FIG. 2 is a schematic cross-sectional view of another exemplary device.

Referring to FIG. 2, in many embodiments, the adaptor 108 further comprises at least one rib 101 formed on an interior surface 103 of the adaptor 108. Advantageously, the inclusion of one or more ribs can effectively minimize contact between an open end of a lumened or cannulated device and the interior surface of the adaptor, and thereby minimize blocking flow of a fluid sample out of the lumened or cannulated device. Such one or more ribs may be integrally molded on the interior surface of the adaptor during fabrication of the adaptor. In select embodiments, the filter holder 102 comprises a tubular shape comprising a length L and a width W, wherein the length L is at least three times greater than the width W. Providing a long tubular shape may allow the device to be used in commercially available detection systems, for instance a luminometer configured to interface with a tubular cuvette.

The size of the adaptor is not particularly limited. The adaptor usually comprises a volume of at least 5 milliliters, or at least 10 milliliters, or at least 15 milliliters, or at least 20 milliliters. The volume of the adaptor provides space for a length of a lumened or cannulated device to be inserted into the device, as well as to hold a volume of a fluid sample as it is passing from the adaptor into the filter holder. It has been found that the device tends to be effective in decreasing or preventing undesirable movement of a lumened or cannulated device while passing a fluid sample through the device (or during other reprocessing steps) when the lumened or cannulated device is inserted into the adaptor at least a minimum amount, for instance at least 15 millimeters, or at least 20 millimeters, or at least 25 millimeters, or at least 30 millimeters into the adaptor through the aperture in an end of the adaptor. In such embodiments, the adaptor comprises a length of at least 20 millimeters, or at least 30 millimeters, or at least 35 millimeters, to accommodate the length of the lumened or cannulated device.

Figure 3A:
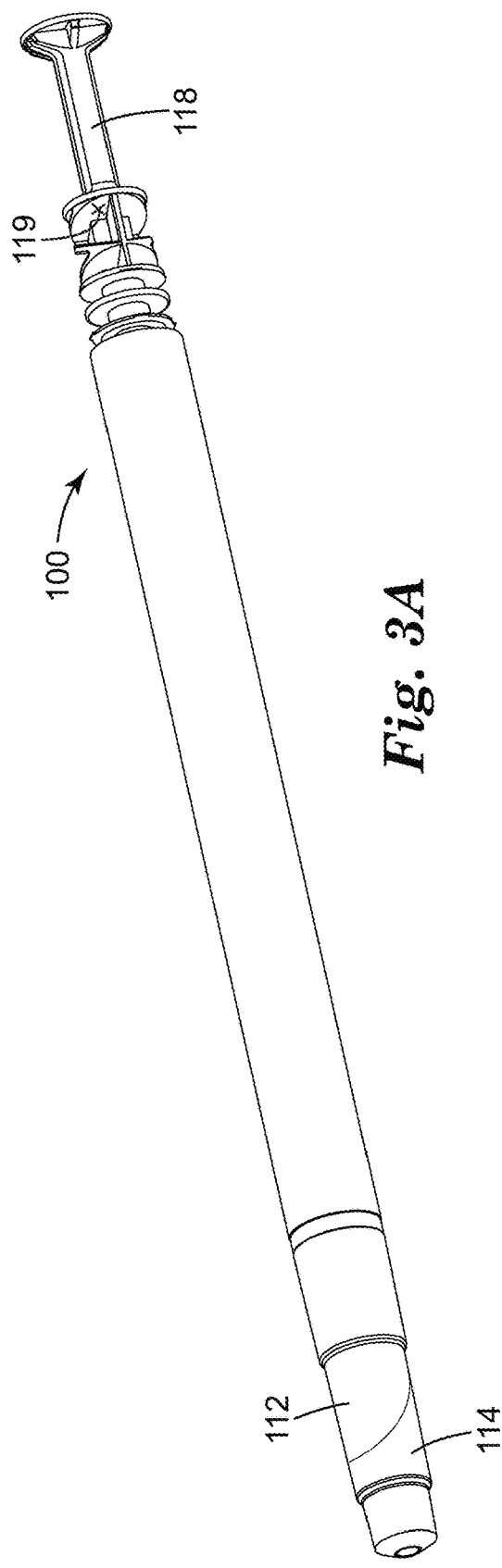
FIG. 3A is a schematic perspective view of a further exemplary device.
Figure 3B:
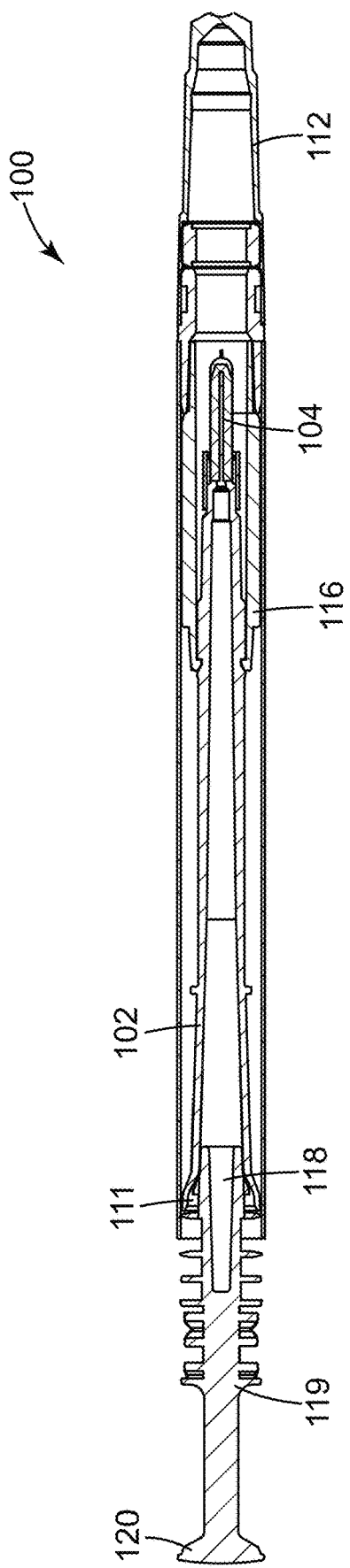
FIG. 3B is a schematic cross-sectional view of the device of FIG. 3A.

Referring now to FIGS. 3A and 3B, a device 100 is shown including a filter holder 102 attached to an adaptor 108, and further comprising a cuvette 112, wherein the tip portion of the filter holder is configured to be inserted into the cuvette 112. In most embodiments, the device 100 includes at least one detection reagent 114 disposed in the cuvette. The cuvette 112 can be formed in a variety of geometric shapes, such as cubic, cuboid, cylindrical, conical, frusto-conical, other suitable geometric shapes, and combinations thereof. Typically, the cuvette 112 integrally provides an outer assay tube into which some or all of the length of the filter holder 102 may be inserted. At least a portion of the walls of the cuvette 112 are configured to allow the passage of light (e.g., visible light) into and/or out of the cuvette 112. For instance, the cuvette is typically fabricated from optically-transmissible material(s) (e.g., glass or a polymeric material such as poyethylene, polypropylene, polycarbonate, or polystyrene, for example) that permits the transmission therethrough of light emitted as a product of a detection reaction.

Figure 4:
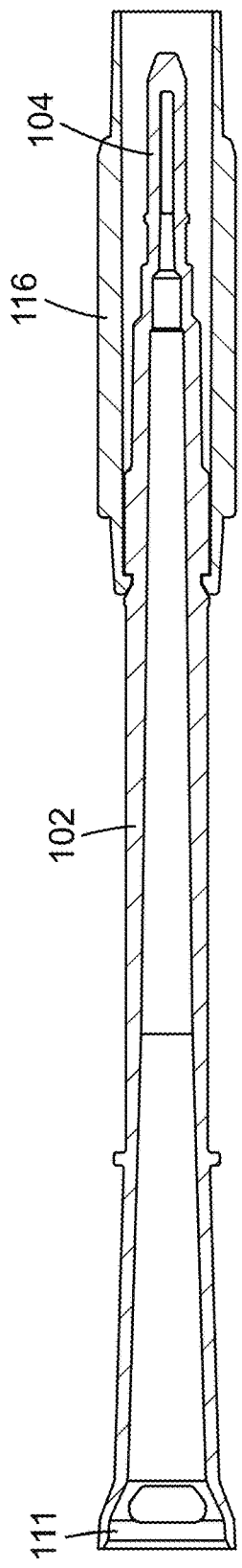
FIG. 4 is a schematic cross-sectional view of an exemplary filter holder with a sleeve.

Referring to FIGS. 3B, 4 and 5, in some embodiments, the filter holder 102 further comprises a sleeve 116 disposed in/on the filter holder 102. Such a sleeve 116 is configured to protect the tip portion 104 and the nonwoven article 106 from contamination during use of the device (e.g., handling of the filter holder 102, etc.). FIG. 4 illustrates the sleeve 116 preventing direct contact to the tip portion 104 of any material present outside of the filter holder 102, whereas FIG. 5 shows the tip portion 104 of the filter holder 102 disposed in a cuvette 112 and the sleeve 116 positioned at a distance from the tip portion 104. Hence, in certain embodiments the sleeve 116 is slidably disposed in the filter holder 102 to allow protection of the tip portion 104 and the nonwoven article 106 (not shown in FIG. 3B, 4, or 5), as well as to be moved away from the tip portion 104 and the nonwoven article 106 to avoid contact with the detection reagent 114 in the cuvette 112 (and transfer of any contaminants on the sleeve 116 into the detection reagent).

Referring to FIGS. 3B and 5, in many embodiments, the device 100 further comprises a handle 118 configured to be inserted in an open end 111 of the filter holder 102. In certain embodiments, the handle 118 comprises a feature 119 (or a mark, shown in FIG. 3A) disposed at a distance from an end 120 of the handle 118. Such a feature or mark advantageously indicates to a user a suitable distance to move the handle within the filter holder when contacting the nonwoven article with the detection reagent. Suitable materials from which at least a portion of the handle 118 may be fabricated include the materials described above with respect to the filter holder 102 and adaptor 108. Often, at least a portion of the end 120 of the handle 118 includes a compliant polymer (e.g., silicone) for ease of inserting and removing the handle 118 from the filter holder 102.

Referring now to FIG. 6, a device 100 is shown, which includes a lumened or cannulated device 122 inserted into the adaptor 108 (i.e., through the aperture 110). The device 100 in this embodiment further includes a pressure differential source 124, configured to urge a fluid sample 121 through the lumened or cannulated device 122, through the adaptor 108, through the filter holder 102, and contacting the nonwoven article (not shown) while passing through the device 100. The pressure differential source 124 is not particularly limited, and usually comprises a syringe (shown in FIG. 6), a pump, or an aspirator. Conveniently, in certain embodiments a waste container 126 may be used to collect the fluid sample 121 after it exits the tip portion 104 of the filter holder 102, for proper disposal of the fluid sample 121.

Figure 7A:
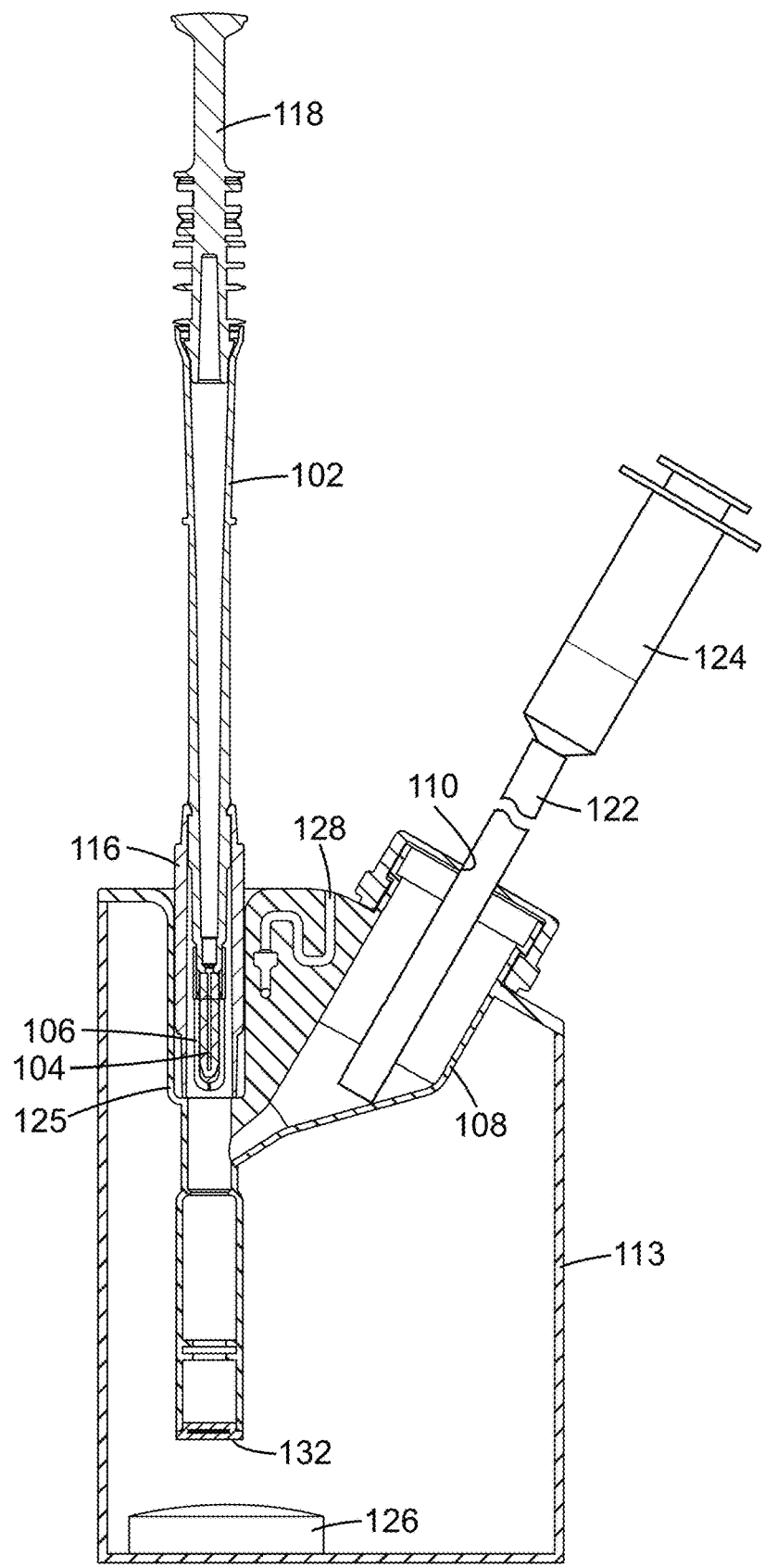
FIG. 7A is a schematic cross-sectional view of a still further exemplary device.
Figure 7B:
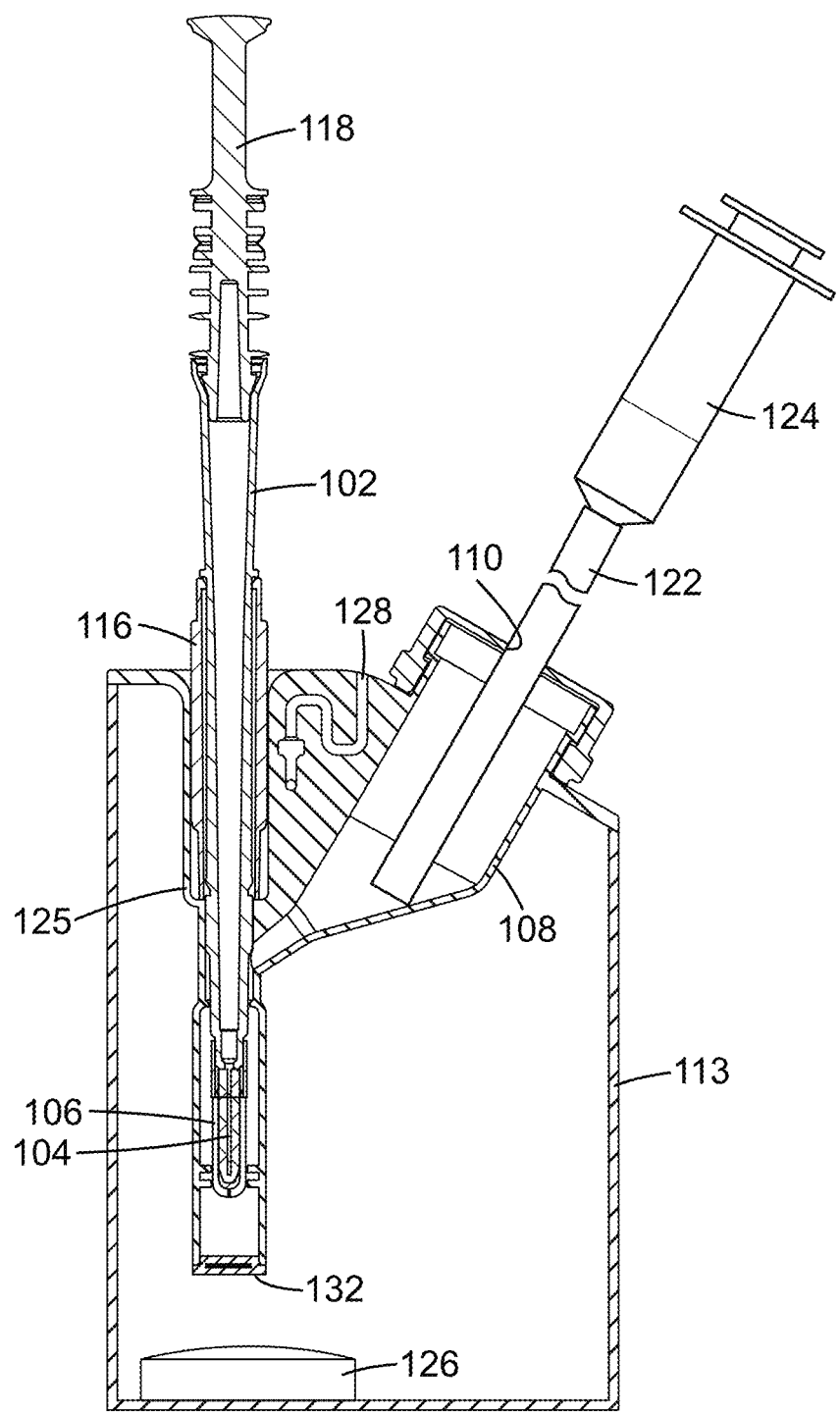
FIG. 7B is a schematic cross-sectional view of the device of FIG. 7A.

Referring to FIGS. 7A and 7B, in at least one embodiment, the device 100 includes the filter holder 102 and the adaptor 108 attached to each other in a Y-shaped configuration. Use of a Y-configuration allows for the device 100 to include the handle 118 integrally formed on the filter holder 102 and attached to the tip portion 104 at the same time that a lumened or cannulated device 122 is inserted into the aperture 110 of the adaptor 108. A nonwoven article 106 is disposed on the tip portion 104 of the filter holder 102. The filter holder 102 further optionally comprises a sleeve 116 which can protect the nonwoven article 106 from contact contamination when the handle 118 is removed from the filter holder 104, and typically the sleeve 116 is configured to slide up the handle 118 away from the nonwoven article 106 when the filter holder 102 is inserted into a container 125. In certain embodiments, the filter holder further includes at least one seal feature to provide a seal that prevents a fluid sample from traveling up the filter holder in a direction away from the nonwoven article. The device 100 thus comprises 1) a filter holder 102, the filter holder 102 comprising a tip portion 104; 2) a nonwoven article 106 disposed on the tip portion 104 of the filter holder 106; 3) a container 125 configured to hold the filter holder 102; and 4) an adaptor 108 attached to the container 125 in a Y-shaped configuration, the adaptor 108 defining an aperture 110.

The container 125 further includes a one-way valve 132 (e.g., a one-way check valve) through which a fluid sample 121 may flow out of the container 125, but through which nothing may flow into the container 125. As illustrated in FIGS. 7A and 7B, the device 100 may further comprise a housing 113 configured to accept and support the Y-shaped configured device 100. For convenience, the housing 113 optionally further includes a waste collection container 126, and a vent 128 to allow pressure from a pressure differential source to exit the housing 113. In an embodiment, the waste collection container comprises an absorbent material (e.g., a superabsorbent polymer) to prevent leakage of the fluid sample from the device during use and disposal. Further, an antibacterial material could also be incorporated into the waste collection container to minimize the presence of live microorganism strains and/or cellular analytes following sampling.

Methods

Figure 8:
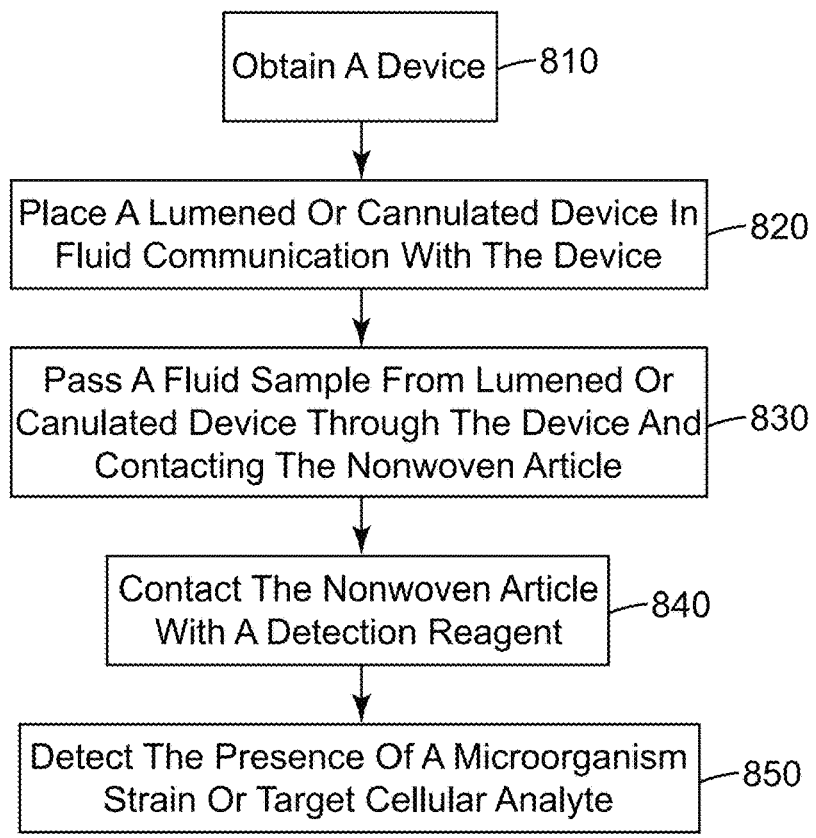
FIG. 8 is a flow chart of an exemplary method.

In a second aspect, a method of detecting at least one microorganism strain or target cellular analyte in a fluid sample is provided. The method includes obtaining a device; placing a lumened or cannulated device in fluid communication with the device; and passing a fluid sample suspected of containing at least one microorganism strain or target cellular analyte from the lumened or cannulated device through the device and contacting the nonwoven article. The method further comprises contacting the nonwoven article with at least one detection reagent and detecting the presence of the at least one microorganism strain or target cellular analyte concentrated by the nonwoven article. The device is according to the various embodiments of the first aspect described in detail above. Referring to FIG. 8, the method includes obtaining a device 810; placing a lumened or cannulated device in fluid communication with the device 820; passing a fluid sample suspected of containing at least one microorganism strain or target cellular analyte from the lumened or cannulated device through the device and contacting the nonwoven article 830; contacting the nonwoven article with at least one detection reagent 840; and detecting the presence of the at least one microorganism strain or target cellular analyte concentrated by the nonwoven article 850.

Referring back to FIGS. 1A, 1B, 3A, and 4-7, in certain embodiments, the method comprises obtaining a device 100; placing a lumened or cannulated device 122 in fluid communication with the device 100; and passing a fluid sample 121 suspected of containing at least one microorganism strain or target cellular analyte from the lumened or cannulated device 122 through the device 100 and contacting the nonwoven article 106. The method further comprises contacting the nonwoven article 106 with at least one detection reagent 114 and detecting the presence of the at least one microorganism strain or target cellular analyte concentrated by the nonwoven article 116. The device 100 comprises 1) a filter holder 102, the filter holder 102 comprising a tip portion 104; 2) a nonwoven article 106 disposed on the tip portion 104 of the filter holder 102; and 3) an adaptor 108 attached to the filter holder 102, the adaptor 108 defining an aperture 110.

In certain embodiments, the lumened or cannulated device 122 is placed in fluid communication with the device 100 by inserting the lumened or cannulated device 122 through the aperture 110 of the adaptor 108, wherein at least a predetermined length of the lumened or cannulated device 122 is disposed inside the adaptor 108 (e.g., at least 25 millimeters). In configurations in which the filter holder 102 and the adaptor 108 are attached in series, typically the lumened or cannulated device 122 is removed from being in fluid communication with the device 100, the adaptor 108 is disconnected from the filter holder 102, and a handle 118 is inserted into the filter holder 102 and attached to the tip portion 104 of the filter holder 102 prior to contacting the nonwoven article 106 with the at least one detection reagent 114.

Figure 9:
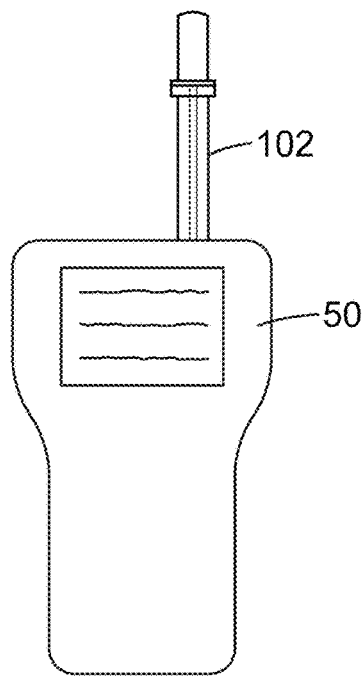
FIG. 9 is a schematic side view of an exemplary filter holder operationally coupled to a luminometer.
Figure 10:
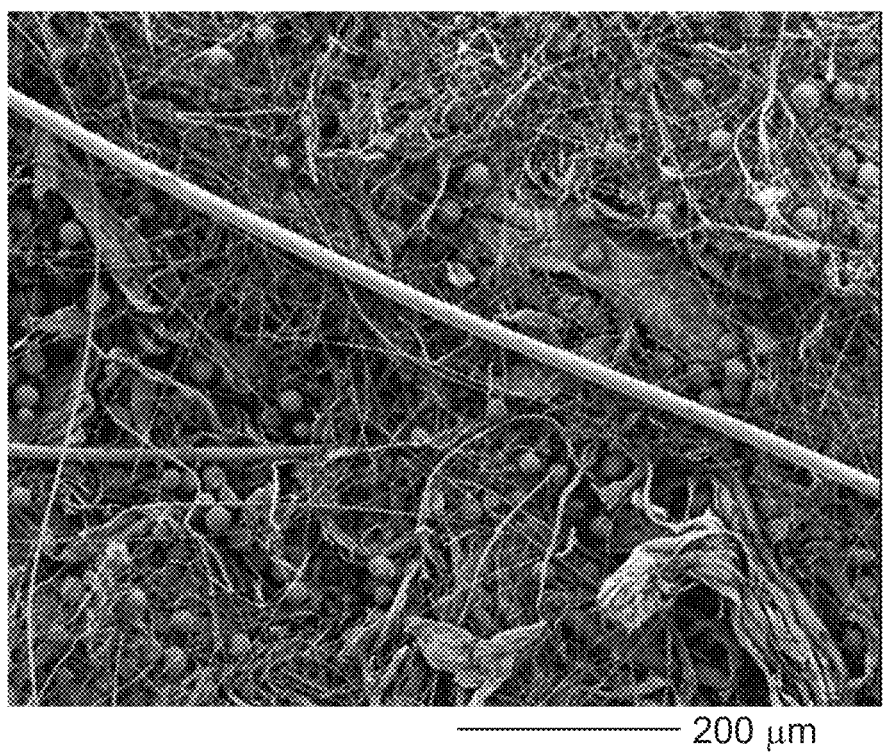
FIG. 10 is a scanning electron microscope (SEM) image of the exemplary nonwoven article of Example 1.

In most embodiments, the device 100 further comprises a cuvette 112 containing the at least one detection reagent 114, wherein the cuvette 112 is operationally coupled to a luminometer 50 (referring also to FIG. 9) prior to detecting the presence of the at least one microorganism strain or target cellular analyte concentrated by the nonwoven article 106. Commercially-available luminometers are suitable for use in any embodiment of the present disclosure. A non-limiting example of a suitable luminometer is the 3M CLEAN-TRACE NG Luminometer commercially available from 3M Company, St. Paul, Minn. Typically, the cuvette 112 is operationally coupled by inserting a portion (e.g., the cuvette portion) of the filter holder 102 or the entire filter holder 102 into a corresponding receiving compartment of the luminometer 50.

A typical volume of a fluid sample 121 passed through the device 100 is at least 20 milliliters, or at least 30 milliliters, or at least 40 milliliters, or at least 50 milliliters, or at least 75 milliliters, or at least 100 milliliters, or even at least 125 milliliters of the fluid sample 121. The greater the volume of the fluid sample 121, the more fluid may be sampled, while the lower the volume of the fluid sample 121, the faster the full volume of the fluid sample 121 may be passed through the device 100.

In many embodiments, the fluid sample 121 comprises a rinsate from the lumened or cannulated device 122. As discussed above, a rinsate from a lumened or cannulated device can be used to determine whether or not the lumened or cannulated device has been sufficiently cleaned (e.g., cleaned enough to meet a predetermined standard of cleanliness). The rinsate may be a rinsate obtained after a cleaning process (e.g., reprocessing of a medical instrument) or after a reprocessed lumened or cannulated device has been stored but prior to further use. In some embodiments, the lumened or cannulated device 122 comprises a medical device undergoing reprocessing. Suitable lumened or cannulated devices comprise a flexible endoscope, a semi-rigid endoscope, a rigid endoscope, a laparoscopic instrument, or a cannulated robotic surgical instrument.

A variety of microorganisms can be concentrated and detected according to the present disclosure, including, for example, bacteria, fungi, yeasts, protozoans, viruses (including both non-enveloped and enveloped viruses), fungal spores, bacterial endospores (for example, *Bacillus* (including *Bacillus anthracis, Bacillus cereus*, and *Bacillus subtilis*) and *Clostridium* (including *Clostridium botulinum, Clostridium difficile*, and *Clostridium perfringens*)), and the like, and combinations thereof, such as gram-negative bacteria, gram-positive bacteria, yeasts, fungi, and combinations thereof. Target cellular analyte that can be concentrated and detected by using the methods of the disclosure include nucleic acids, proteins, adenosine triphosphate (ATP), or combinations thereof.

In certain embodiments, the method further comprises washing the at least one microorganism strain- or target cellular analyte-bound nonwoven article prior to contacting the at least one microorganism strain- or cellular analyte-bound nonwoven article with at least one detection reagent. It has been discovered that contaminants such as residual sample matrix can be removed from the nonwoven article without significant loss of the bound or captured microorganisms and/or cellular analytes. In certain embodiments, washing includes for instance and without limitation, rinsing with sterile deionized water or bottled drinking water, or rinsing with aqueous salt or buffer solutions. Washing the nonwoven article tends to remove components that could otherwise interfere with detecting the presence of the bound microorganisms and/or cellular analytes, depending on the particular detection method employed.

It is an advantage of embodiments of the present disclosure that the nonwoven article 106 concentrates microorganism strains and/or target cellular analytes from the fluid sample 121, decreasing the minimum concentration of such strains and/or analytes in the fluid sample 121 that can successfully be detected. To detect the at least one microorganism strain or target cellular analyte, the nonwoven article 106 is placed into contact with at least one detection reagent 114. It has been found that the method of contacting the nonwoven article 106 with the detection reagent 114 can impact the sensitivity of the detection. Suitable methods of contacting the nonwoven article with the at least one detection reagent include an up-and-down or a back-and-forth motion of the nonwoven article with respect to the at least one detection reagent, vortexing the at least one detection reagent and the nonwoven article, manual agitation of the nonwoven article and the at least one detection reagent, or any combination thereof. Examples 21L-21O below show differences in the contacting (e.g., agitating) method according to specific contacting conditions. The skilled practitioner is capable of selecting one or more of these disclosed contacting methods to effectively transfer a sufficient portion of the at least one microorganism strain or target cellular analyte concentrated on the nonwoven article to the at least one detection reagent.

As noted above, the fluid sample 121 is optionally passed through the device 100 using a pressure differential, such as using a syringe 124, a pump, or an aspirator. Depending on the particular device configuration, the pressure differential may comprise either positive pressure or negative pressure. It has been discovered that use of the present devices allows for achievement of a low pressure drop during passing of a fluid sample 121 through the device 100. For instance, a difference in pressure of the fluid sample 121 entering the device 100 and exiting the device 100 is optionally no greater than 20 kilopascals. Similarly, a fast flow rate may be achieved in part due to the low pressure drop. In certain embodiments, the flow rate of the fluid sample 121 through the device 100 is at least 2 milliliters per minute, or at least 5 milliliters per minute, or at least 7 milliliters per minute, or at least 10 milliliters per minute, or at least 15 milliliters per minute, or at least 40 milliliters per minute, or at least 60 milliliters per minute, or at least 80 milliliters per minute and a difference in pressure of the fluid sample 121 entering the device 100 and exiting the device 100 is no greater than 20 kilopascals. In an embodiment of the present disclosure, passing the fluid sample through the device occurs at a pressure of 14.7 pounds per square inch (psi) (101.3 kilopascals (kPa)) or less, or 4.0 pounds per square inch (psi) (27.58 kilopascals (kPa)) or less, or 3.0 psi (20.68 kPa), or 2.0 psi (13.79 kPa), or 1.0 psi (6.9 kPa), or 0.9 psi (6.21 kPa), or 0.8 psi (5.52 kPa), or 0.7 psi (4.83 kPa), or 0.6 psi (4.14 kPa), or even 0.5 psi (3.45 kPa) or less, and at a pressure of at least 0.4 psi (2.76 kPa), or at least 0.5 psi (3.45 kPa).

In certain embodiments, placing the microorganism strain- or target cellular analyte-bound nonwoven article in contact with a reagent includes placing at least a portion of the filter holder (including the nonwoven article on the tip portion of the filter holder) in a receptacle that comprises a material through which a detection signal can be detected, wherein the receptacle contains at least one reagent. For instance, placing the microorganism strain- or target cellular analyte-bound nonwoven article in contact with a reagent optionally includes placing the filter holder in a receptacle (e.g., a cuvette) configured to be operationally connected to a luminometer, wherein the receptacle contains at least one reagent. Hence, in such an embodiment, detection is facilitated by disposing the receptacle in the luminometer for measurement of light generated from reaction of the bound microorganism strain and/or target cellular analyte with at least one reagent.

Similarly, the receptacle can be interfaced with other types of equipment depending on the particular detection method. It has been discovered that microorganism strain and/or target cellular analyte can be detected without requiring removal from being captured by the nonwoven article. The ability to detect microorganism strains and/or target cellular analytes attached to the nonwoven article is advantageous because it decreases the number of required method steps as compared to methods in which the microorganism strains and/or target cellular analytes need to be eluted from a nonwoven article prior to detection. Further, the nonwoven article concentrates the microorganism strains and/or target cellular analytes into the volume of the article, which is typically significantly smaller than the volume of the fluid sample contacted with the nonwoven article.

In a fifth aspect, and referring again to FIGS. 7A and 7B, a method of detecting at least one microorganism strain or target cellular analyte in a fluid sample is provided, including obtaining a device 100 comprising a Y-shaped configuration. The device comprises 1) a filter holder 102, the filter holder comprising a tip portion 104; 2) a nonwoven article 106 disposed on the tip portion 104 of the filter holder 102; 3) a container 125 configured to hold the filter holder 102; and 4) an adaptor 108 attached to the container 125 in a Y-shaped configuration, the adaptor 108 defining an aperture 110. The method further comprises placing a lumened or cannulated device 122 in fluid communication with the device 100; and passing a fluid sample suspected of containing at least one microorganism strain or target cellular analyte from the lumened or cannulated device through the device 100, such as through the adaptor 108, into the filter holder 102, and contacting the nonwoven article 106. The method additionally comprises contacting the nonwoven article with at least one detection reagent and detecting the presence of the at least one microorganism strain or target cellular analyte concentrated by the nonwoven article. Typically, the nonwoven article is contacted with the detection reagent by removing the filter holder from the device and inserting the filter holder into a container holding the at least one detection reagent.

The type of container employed will depend on the detection method (e.g., a cuvette for luminescence-based methods).

Microorganisms and/or cellular analytes that have been captured or bound (for example, by adsorption, absorption, or by sieving) by the nonwoven article can be detected by essentially any desired method that is currently known or hereafter developed. Such methods include, for example, culture-based methods, microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism and/or cellular analyte capture optionally can include washing to remove sample matrix components, staining, boiling or using elution buffers or lysis agents to release cellular analyte from the concentration device, or the like.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification). The captured or bound microorganisms can be lysed to render their genetic material (e.g., cellular analytes) available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.). Bioluminescence detection methods for ATP often include the known luciferin-luciferase system in which luciferase enzyme catalyzes the oxidation of luciferin in the presence of ATP and a divalent cation (such as magnesium or calcium). Other luminescence-based detection methods can also be utilized.

In many embodiments, detection comprises a culture-based detection method, an imaging detection method, a fluorescence-based detection method, a colorimetric detection method, an immunological detection method, a genetic detection method, a bioluminescence-based detection method, or a combination thereof.

Kits and Systems

In a third embodiment, a kit is provided. The kit includes a device; a cuvette containing at least one detection reagent; and a handle configured to be inserted into the filter holder. The device is according to various embodiments of the first aspect described in detail above. Referring again to FIGS. 1A, 1B, 3A, and 4-7, kit includes a device 100; a cuvette 112 containing at least one detection reagent 114; and a handle 118 configured to be inserted into the filter holder 102 of the device 100. The device includes 1) a filter holder 102, the filter holder 102 comprising a tip portion 104; 2) a nonwoven article 106 disposed on the tip portion 104 of the filter holder 102.

As shown in FIG. 6, in certain embodiments the kit further includes a stand 130 configured to hold the device 100. The stand 130 not only frees up a hand of the user of the device 100, but also can secure the device 100 in a desirable position (e.g., at an angle that does not require substantial bending of the lumened or cannulated device 122). Moreover, in some embodiments the kit includes a pressure differential source (e.g., a syringe 124, a pump, or an aspirator). The kit typically further includes instructions for using the kit to detect at least one microorganism strain or target cellular analyte in a fluid sample.

In a fourth aspect, a system is provided. The system includes a device; a cuvette containing at least one detection reagent; a handle configured to be inserted into the filter holder; and a luminometer. The device is according to various embodiments of the first aspect described in detail above. Referring again to FIGS. 1A, 1B, 3A, 4-7, and 9, the system includes a device 100; a cuvette 112 containing at least one detection reagent 114; a handle 118 configured to be inserted into the filter holder 102; and a luminometer 50. The system typically further includes instructions for using the system to detect at least one microorganism strain or target cellular analyte in a fluid sample.

In certain embodiments, the system further includes one or more of a lumened or cannulated device 122, a stand 130 configured to hold the device 100, and a pressure differential source (e.g., comprising a syringe 124, a pump, or an aspirator).

In a sixth aspect, another kit is provided. The kit comprises a device comprising a Y-shaped configuration; a cuvette containing at least one detection reagent; and a handle configured to be inserted into the filter holder. For instance, referring again to FIGS. 7A and 7B, the kit includes a device 100 comprising a Y-shaped configuration and a handle 118 configured to be inserted into the filter holder 102. In a seventh aspect, another system is provided. The system comprises a device comprising a Y-shaped configuration; a cuvette containing at least one detection reagent; a handle configured to be inserted into the filter holder; and a luminometer. The device comprises 1) a filter holder 102, the filter holder comprising a tip portion 104; 2) a nonwoven article 106 disposed on the tip portion 104 of the filter holder 102; 3) a container 125 configured to hold the filter holder 102; and 4) an adaptor 108 attached to the container 125 in a Y-shaped configuration, the adaptor 108 defining an aperture 110.

In many embodiments the kit and/or system further includes a housing 113 configured to hold each of the filter holder 102 and the adaptor 108. An advantage of employing such a housing is the capability of keeping the device self-contained in the housing and only removing the filter holder and the lumened or cannulated device from the device during/following use. In certain embodiments, the kit and/or system further comprises a pressure differential source 124 comprising a syringe (shown in FIG. 7B), a pump, or an aspirator. Instructions are often included for using the kit or system to detect at least one microorganism strain or target cellular analyte in a fluid sample.

Nonwoven Articles

In certain embodiments, the nonwoven article includes a fibrous porous matrix. In certain embodiments, the nonwoven article includes a) a fibrous porous matrix and b) a plurality of concentration agent particles enmeshed in the fibrous porous matrix. The fibrous porous matrix optionally consists essentially of inorganic fibers and polymeric fibers. The nonwoven fibrous porous matrix is often in the form of a layer of interlaid fibers that are not woven or knitted together. The nonwoven, fibrous porous matrix can be prepared by any suitable process such as, for example, air laying techniques, spunlaid techniques such as meltblowing or spunbonding, carding, wetlaying, and combinations thereof. In many embodiments, the fibrous nonwoven matrix is prepared by wetlaid techniques.

Fibers suitable for use in preparing the nonwoven fibrous porous matrix are usually pulpable or extrudable fibers such as those that are stable to radiation and/or to a variety of solvents. Optionally, at least some of the polymeric fibers can be selected to exhibit a degree of hydrophilicity. Useful fibers include polymeric fibers, inorganic fibers, and combinations thereof.

More particularly, the fibers include a plurality of different types of fibers, including polyolefin fibers and fiberglass fibers.

Suitable polymeric fibers include those made from natural polymers (those derived from animal or vegetable sources) and/or synthetic polymers, including thermoplastic and solvent-dispersible polymers. Useful polymers include polyolefins (for example, poly(ethylene) (e.g., low density polyethylene, medium density polyethylene, high density polyethylene, etc.), polypropylene, poly(1-butene), copolymers of ethylene and propylene, alpha olefin copolymers such as copolymers of ethylene or propylene with 1-butene, 1-hexene, 1-octene, and 1-decene such as poly(ethylene-co-1-butene), poly(ethylene-co-1-butene-co-1-hexene), and the like); polylactic acid; poly(isoprenes); poly(butadienes); polyamides (for example, nylon 6, nylon 6,6, nylon 6,12, poly(iminoadipoyliminohexamethylene), poly(iminoadipoyliminodecamethylene), polycaprolactam, and the like); polyimides (for example, poly(pyromellitimide) and the like); polyethers; poly(ether sulfones) (for example, poly (diphenylether sulfone), poly(diphenylsulfone-co-diphenylene oxide sulfone), and the like); poly(sulfones); poly (vinyl esters) such as poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl ethers); poly(vinyl alcohols); polyaramids (for example, para-aramids such as poly (paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); wool; silk; cellulosic polymers (for example, cellulose, cellulose derivatives such as rayon, and the like); acrylic polymers (for example, polyacrylonitrile); polyesters (for example, polyethylene terephthalate); fluorinated polymers (for example, poly(vinyl fluoride), poly(vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; poly(carbonates); and the like; and combinations thereof. In certain embodiments, the polymeric fibers comprise a polyolefin, a polysulfone, a polyamide, or a combination thereof.

Suitable inorganic fibers include those that contain at least one inorganic material selected from glasses, ceramics, and combinations thereof. These fibers are often added to provide strength to the fibrous porous matrix. For example, porous matrix layers containing inorganic fibers are often capable of being bent, folded, or pleated without breaking apart. Useful inorganic fibers include, for example, fiberglass (for example, E-glass, S-glass, and the like), ceramic fibers (for example, fibers made of metal oxides (such as alumina), silicon carbide, boron nitride, boron carbide, and the like), and combinations thereof. Useful ceramic fibers can be at least partially crystalline (exhibiting a discernible X-ray powder diffraction pattern or containing both crystalline and amorphous (glass) phases). In some applications, the inorganic fibers include fiberglass.

To facilitate entrapment of the concentration agent particles and/or to ensure a high surface area, the fibers used to form the nonwoven, fibrous porous matrix often contain at least one fibrillated fiber (for example, in the form of a main fiber surrounded by many smaller attached fibrils). The main fiber generally can have a length in the range of 0.5 millimeters to 5 millimeters and a diameter in a range of 1 micrometer to 20 micrometers. The fibrils typically can have a sub-micrometer diameter. In many embodiments, the fibrillated fibers are prepared from a polyolefin such as poly (ethylene) or polypropylene, or from an acrylic polymer such as polyacrylonitrile.

Suitable polymeric fibers further include bi-component fibers, which typically assist in binding all of the matrix fibers together due to a difference in melting point of one of the materials in the bi-component fiber. Bi-component fibers can have, for example, a core-sheath structure, a side-by-side structure, an islands-in-the-sea structure, or a segmented-pie structure, or the like. An example side-by-side bi-component fiber is the polyolefin thermally bonded bi-component fiber that is commercially available from Chisso Corporation (Osaka, Japan) under the trade designation CHISSO (for example, CHISSO ES). An example core-sheath bi-component fiber is commercially available from Unitika Ltd. (Osaka, Japan) under the trade designation MELTY (for example, MELTY 4080) and those commercially available from Minifibers, Inc. (Johnson City, Tenn.) made of ethyl vinyl acetate (sheath) and polypropylene (core), or made of a co-polyester of polyester and polyethylene terephthalate (PET) (sheath) and polyester (core).

The nonwoven fibrous porous matrix contains a plurality of different types of fibers. In some embodiments, the porous matrix can be formed using three, four, or even more different types of fibers. For example, a fiberglass fiber can be added for strength and integrity, while fibrillated poly (ethylene) can be added for entrapment of the particulates. Additionally, nylon fibers provide hydrophilic character while fibrillated poly(ethylene) fibers provide hydrophobic character to the porous matrix. If fibrillated and non-fibrillated fibers are used in combination, the weight ratio of fibrillated fibers to non-fibrillated fibers is often at least 1:2, at least 1:1, at least 2:1, at least 3:1, at least 5:1, or even at least 8:1. In some embodiments, mixtures of hydrophobic and hydrophilic polymeric fibers are used. For example, the fibrous porous matrix can include a mixture of hydrophobic fibers such as polyolefins plus hydrophilic fibers such as polysulfones. In some specific examples, the polymeric fibers include polyolefin fibers, bi-component fibers, and fiberglass fibers.

In certain embodiments, the fibrous porous matrix is free of polyamide fibers. It has been discovered that the inclusion of nylon fibers in the fibrous porous matrix can result in lower luminescence than the fibrous porous matrix without the nylon fibers for a bioluminescent ATP detection method.

Preferably, the fibers used to form the nonwoven fibrous porous matrix are uncrimped. In contrast to uncrimped fibers, crimped fibers may be identified as displaying repeating features (as manifested e.g., in a wavy, jagged, sinusoidal, etc., appearance of the fiber), by having a helical appearance (e.g., particularly in the case of crimped fibers obtained by thermal activation of bi-component fibers), and the like, and are readily recognizable by those of ordinary skill in the art.

Exemplary crimped fibers are described in U.S. Pat. No. 4,118,531 to Hauser and U.S. Pat. No. 5,597,645 to Pike et al., and CA Patent 2612854 to Sommer et al.

The fibers used to form the nonwoven fibrous porous matrix can be of a length and diameter that can provide a porous matrix having sufficient structural integrity and sufficient porosity for a particular application (for example, passing a fluid sample through the matrix). The fiber lengths are often at least about 0.5 millimeter, at least 1 millimeter, at least 2 millimeters, at least 3 millimeters, at least 4 millimeters, at least 6 millimeters, at least 8 millimeters, at least 10 millimeters, at least 15 millimeters, or at least 20 millimeters, and up to 50 millimeters, up to 40 millimeters, up to 30 millimeters, or up to 25 millimeters. The diameter of the fibers can be, for example, at least 10 micrometers, at least 20 micrometers, or at least 30 micrometers. The fiber lengths and diameters will vary depending upon factors such as the nature of the fiber and the type of application.

The nonwoven fibrous porous matrix often includes a mixture of polyolefin fibers, glass fibers, and bi-component fibers. In some particular embodiments, the nonwoven fibrous porous matrix contains a mixture of fibrillated polyethylene fibers, glass fibers, and sheath-core bi-component fibers. In some examples, the nonwoven fibrous porous matrix contains 40 to 80 weight percent fibrillated polyethylene fibers, 5 to 20 weight percent glass fibers, and 5 to 20 weight percent bi-component fibers. In some examples, the nonwoven fibrous porous matrix contains 40 to 80 weight percent fibrillated polyethylene fibers, 10 to 30 weight percent nylon fibers, 5 to 20 weight percent glass fibers, and 5 to 20 weight percent bi-component fibers. In other examples, the nonwoven, fibrous porous matrix contains 50 to 70 weight percent fibrillated polyethylene fibers, 5 to 15 weight percent glass fibers, and 5 to 20 weight percent bi-component fibers. In still other examples, the fibrous porous matrix contains 55 to 65 weight percent fibrillated polyethylene fibers, 0 to 20 weight percent nylon fibers, 5 to 15 weight percent glass fibers, and 10 to 20 weight percent bi-component fibers.

As noted above, the fibrous porous matrix often consists essentially of inorganic fibers and polymeric fibers. Accordingly, in most embodiments, the fibrous porous matrix contains only fibers. For example, at least 90 weight percent, at least 95 weight percent, at least 98 weight percent, at least 99 weight percent, or at least 99.5 weight percent of a dry fibrous porous matrix is fibers. In certain embodiments, the nonwoven article comprises a thickness of at least 0.1 millimeters, or at least 0.15 millimeters, or at least 0.2 millimeters, or at least 0.3 millimeters, or at least 0.4 millimeters, or at least 0.5 millimeters, or at least 0.6 millimeters. The nonwoven article usually comprises a thickness of up to 1 millimeter, or up to 0.9 millimeters, or up to 0.8 millimeters, or up to 0.7 millimeters, or up to 0.55 millimeters. Stated differently, the nonwoven article may comprise a thickness of between 0.15 millimeters and 1 millimeter, or between 0.15 millimeters and 0.8 millimeters, or between 0.1 millimeters and 0.7 millimeters. In certain embodiments, a nonwoven article having a thickness towards the lower end of the thickness range is selected to minimize interference with detection of the microorganisms and/or cellular analytes, such as decreasing time required for a reagent to diffuse into the nonwoven article, or decreasing blockage of a generated detection signal.

The nonwoven article typically includes both the fibrous porous matrix and concentration agent particles distributed within the fibrous porous matrix. In most embodiments, the nonwoven article contains at least 10 weight percent concentration agent particles based on a total dry weight of the nonwoven article. If the amount of the concentration agent particles is lower than about 10 weight percent, the nonwoven article may not contain enough concentration agent particles to effectively capture microorganisms or cellular analytes from a fluid sample. In some examples, the nonwoven article contains at least 15 weight percent, at least 20 weight percent, at least 25 weight percent, or at least 30 weight percent concentration agent particles based on a total dry weight of the nonwoven article.

On the other hand, the nonwoven article usually contains no greater than 55 weight percent concentration agent particles based on the total dry weight of the nonwoven article. If the amount of the concentration agent particles is greater than about 55 weight percent, the nonwoven article may contain an insufficient amount of the fibrous porous matrix. That is, the strength of the nonwoven article may be insufficient to hold together when employed to capture microorganism strains and/or target cellular analytes. In some examples, the nonwoven article contains no greater than 50 weight percent, no greater than 45 weight percent, or no greater than 40 weight percent concentration agent particles based on a total weight of the nonwoven article.

Stated differently, the nonwoven article often contains 10 to 55 weight percent concentration agent particles and 45 to 90 weight percent fibrous porous matrix, 15 to 50 weight percent concentration agent particles and 50 to 85 weight percent fibrous porous matrix, 20 to 50 weight percent concentration agent particles and 50 to 80 weight percent fibrous porous matrix, 20 to 45 weight percent concentration agent particles and 55 to 80 weight percent fibrous porous matrix, 25 to 40 weight percent concentration agent particles and 60 to 75 weight percent fibrous porous matrix, or 30 to 40 weight percent concentration agent particles and 60 to 70 weight percent fibrous porous matrix. The amounts are based on the total dry weight of the nonwoven article.

In many embodiments, the nonwoven article (when dry) contains only concentration agent particles and fibrous porous matrix. For example, the nonwoven article typically contains at least 90 weight percent, at least 95 weight percent, at least 98 weight percent, at least 99 weight percent, or at least 99.5 weight percent combined concentration agent particles and fibrous porous matrix when dry.

Concentration agent particles are water-insoluble particulate materials that have been employed to non-specifically capture microorganism strains, cellular analytes, or a combination thereof, when contacted with fluid samples containing microorganisms and/or cellular analytes.

The concentration agent particles typically comprise microparticles. The concentration agent particles typically comprise particles selected from the group consisting of amorphous metal silicates, guanidine-functionalized metal silicates, diatomaceous earth, surface-modified diatomaceous earth, guanidine-functionalized diatomaceous earth, gamma-FeO(OH), metal carbonates, metal phosphates, silica, perlite, guanidine-functionalized perlite, and combinations thereof.

In an embodiment, the concentration agent particles comprise particles of amorphous metal silicates, such as amorphous, spheroidized magnesium silicate, amorphous, spherical aluminum silicate, or a combination thereof. Amorphous, at least partially fused particulate forms of metal silicate can be prepared by any of the known methods of melting or softening relatively small feed particles (for example, average particle sizes up to about 25 micrometers) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle et al.). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate was commercially available for use in cosmetic formulations (for example, "3M COSMETIC MICROSPHERES CM-111", available from 3M Company, St. Paul, Minn.). 3M COSMETIC MICROSPHERES CM-111 have a particle density of 2.3 g/cc, a surface area of 3.3 m²/g, and have a particle size of: 90 percent less than 11 microns (i.e., $D_{90}=11$), 50 percent less than 5 microns, and 10 percent less than 2 microns. Amorphous, spherical aluminum silicate is commercially available for use in paints, primers, powder coatings, and other coatings, for example, "3M CERAMIC MICROSPHERES" from 3M Company, St. Paul, Minn. The 3M CERAMIC MICROSPHERES are alkali alumino silicate ceramic microspheres shaped as solid spheres with particle density of 2.4 g/cc, and are commercially available in three grades: W-210, W-410, and W0610. W-210 particles have a surface area of 5 m²/cc and a particle size of: 95 percent less than about 12 microns (i.e., $D_{95}=12$), 90 percent less than about 9 microns, 50 percent less than about 3 microns, and 10 percent less than about 1 micron. W-410 particles have a surface area of 3 m²/cc and a particle size of: 95 percent less than about 24 microns (i.e., $D_{95}=24$), 90 percent less than about 15 microns, 50 percent less than about 4 microns, and 10 percent less than about 1 micron. W-610 particles have a surface area of 3 m²/cc and a particle size of: 95 percent less than about 40 microns (i.e., $D_{95}=40$), 90 percent less than about 28 microns, 50 percent less than about 10 microns, and 10 percent less than about 1 micron.

In certain embodiments, the concentration agent particles comprise perlite particles. Perlite is a naturally-forming amorphous volcanic glass, containing about 70-75% silicon dioxide and 12-15% aluminum oxide, as well as smaller amounts of other metal oxides, including sodium oxide, potassium oxide, iron oxide, magnesium oxide, and calcium oxide. When perlite is expanded by heat it forms a lightweight aggregate. Examples of suitable perlite particles include the 4106 grade material, the 4156 grade material, and the 476 grade material, all commercially available from Dicaperl Minerals Corporation (Crawfordsville, Ind.).

In certain embodiments, the concentration agent particles comprise guanidine-functionalized metal silicate particles, guanidine-functionalized diatomaceous earth particles, or guanidine-functionalized perlite particles. A guanidine-functionalized particle can be made, for example, according to methods disclosed in commonly assigned International Application No. PCT/US2014/040861 (Kshirsagar et al.). A guanidine-functionalized metal silicate particle, guanidine-functionalized diatomaceous earth particle, or guanidine-functionalized perlite particle comprises at least one guanidine-containing ligand. The guanidine-containing ligand is formed by modifying the metal silicate or perlite particle with a guanidine-containing silane having the structure shown in Formula 1:

$$X_{3-n}R^a{}_nSi\text{—}Y\text{-}G \qquad \text{Formula 1}$$

In Formula 1, Si is a silicon atom, and G denotes a guanidine group of the formula —NH—C(=NH)—NH₂. Y is a divalent group that is covalently bonded to the silicon atom at one end and to the G group at the other end. Each $R^a$ group, if any are present, is independently an alkyl, aralkyl, or aryl group, and is attached to the silicon atom. Each X is a leaving group covalently bonded to the silicon atom and is independently alkoxy or acyloxy, and n is 0, 1, or 2. A typical alkylene can be up to 20, up to 16, 12, 10, 8, 7, 6, 5, 4, or even up to 3 carbons, or even 2 carbons, inclusive of the terminal atoms of the divalent group. In some embodiments, Y is a divalent group comprising an alkylene of 3 to 6 carbons. In a preferred embodiment, Y is a divalent group having 3 carbons (i.e., propyl).

In Formula 1, each leaving group X is independently an alkoxy group of 1, 2, 3, 4, 5, 6, 7, 8, 9, or even up to 10 carbons, or is an acyloxy group of 2 carbons, or 3, 4, 5, 6, 7, 8, 9, or even up to 10 carbons, where the alkoxy or acyloxy group is bonded to the silicon through an oxygen atom.

In some embodiments, n is 0. When n is 0, no $R^a$ groups are present, and Formula 1 can be re-written more simply as shown in Formula 2 (where Si, G, Y, and X are as defined for Formula 1):

$$X_3Si\text{—}Y\text{-}G \qquad \text{Formula 2}$$

When the silane of Formula 1 (or Formula 2) reacts with an —OH group on the surface of a metal silicate, diatomaceous earth, or perlite particle, at least one X leaving group is replaced by a covalent bond of between the silicon atom and an oxygen atom on the surface of the metal silicate or perlite particle. An embodiment of a guanidine-functionalized metal silicate, diatomaceous earth or perlite particle comprising a specific exemplary guanidine-containing ligand within the general type represented by Formula 1, wherein n=0 (i.e., as in Formula 2), is shown in Formula 3 (the circle in Formula 3 represents a metal silicate or perlite particle):

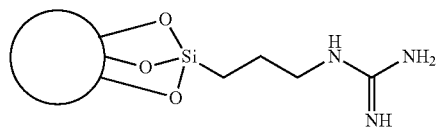

Formula 3

It will be understood that Formula 3 represents a specific embodiment wherein n is 3 and Y is a divalent group that is alkylene having 3 carbons. In each of Formulas 1 to 3, the ionization state of the guanidine group is omitted; however, it will be understood that in various environments such guanidine groups may be charged or uncharged (e.g., protonated or deprotonated), for example, according to the pH of a liquid medium in which the guanidine group is present.

The covalent bond(s) between the oxygen(s) of the ligand and the particle can be conveniently obtained, for example, by reacting a Si-bonded hydrolyzable group of the guanidine-containing precursor with a hydroxyl group of the particle. While the exemplary structure of Formula 3 shows three such bonded oxygen atoms (i.e., n=3 in Formula 1), it will be appreciated that in various embodiments one, two or three such bonded oxygen atoms can be provided. If less than three such oxygen atoms are bonded to the silicon atom, other substituents (e.g., substituents that are not bonded to the particle, and which are not shown in Formula 1) may be present on the silicon atom. For example, the guanidine-containing ligand can include a polymeric structure involving formation of Si—O—Si (i.e., siloxane) groups, resulting from Si—O bonds being formed between two or more guanidine-containing ligand precursors. Without being bound by theory, it is thought that Si—O—Si groups may form in the presence of added water, or other aqueous solvents, or other agent that can hydrolyze bonds in Si—O—R groups, to give rise to more complex guanidine-containing ligand structures attached to particles.

A network of polymerized guanidine-containing ligands can form a coating on the surface of the metal silicate, diatomaceous earth, or perlite particle. In some embodiments it may be desirable to obtain the particle functionalized with polymerized guanidine-containing ligand (e.g., having at least one Si—O—Si group in the polymerized guanidine-containing ligand), as a means of increasing the loading of nitrogen-containing guanidine groups on the surface of the metal silicate, diatomaceous earth, or perlite particle. It is thought that in at least these types of polymerizations, a loading of nitrogen-containing guanidine groups on the surface of the metal silicate, diatomaceous earth, or perlite particle can attain levels of surface nitrogen content in a range from 1 to 10 atomic percent, as can be measured, for example, by X-ray photoelectron spectroscopy.

Guanidine-functionalized particles of the present disclosure include metal silicate particles, diatomaceous earth particles, and perlite particles. Useful metal silicates include silicates of metals such as magnesium, calcium, zinc, aluminum, iron, titanium, and the like (preferably, magnesium and aluminum), and combinations thereof. Preferred are amorphous metal silicates in at least partially fused particulate form. In certain embodiments, more preferred are amorphous, spheroidized metal silicates; and even more preferably, amorphous, spheroidized magnesium silicate. In certain embodiments, more preferred are amorphous aluminum silicates. Metal silicates are known and can be chemically synthesized by known methods or obtained through the mining and processing of raw ores that are naturally-occurring. The metal silicate particle, such as a magnesium silicate particle, bears sufficient surface hydroxyl groups (typically, Si—OH groups) to enable a desired number of guanidine-containing ligands to be covalently attached thereto. Useful perlites include the 4106, 4156, and 476 grade materials from Dicaperl Minerals Corporation (Crawfordsville, Ind.). Useful diatomaceous earth particles can be obtained from natural sources, and are commercially available from Alfa Aesar (A Johnson Matthey Company, Ward Hill, Mass.) or Dicaperl Minerals Corporation (Crawfordsville, Ind.).

The guanidine-functionalized metal silicate, diatomaceous earth, or perlite particles used in nonwoven articles of the present disclosure can be used in essentially any particulate form (preferably, a relatively dry or volatiles-free form) that is amenable to blending with fibers to form the nonwoven articles of the present disclosure. Preferably, the guanidine-functionalized particles are used in the form of a powder. Useful powders include those that comprise microparticles (preferably, microparticles having a particle size in the range of about 1 micrometer (more preferably, about 2 micrometers; even more preferably, about 3 micrometers; most preferably, about 4 micrometers) to about 100 micrometers (more preferably, about 50 micrometers; even more preferably, about 25 micrometers; most preferably, about 15 or 20 micrometers; where any lower limit can be paired with any upper limit of the range, as referenced above).

XPS is a technique that can provide information about the elemental and chemical (oxidation state and/or functional group) concentrations present on a solid surface. XPS typically provides an analysis of the outermost 3 to 10 nanometers (nm) of the specimen surface. XPS is sensitive to all elements in the periodic table except hydrogen and helium with detection limits for most species in the 0.1 to 1 atomic percent concentration range. In some cases, for example for CM-111 particles, a preferred surface composition assessment conditions for XPS can include a take-off angle of 90 degrees measured with respect to the sample surface with a solid angle of acceptance of ±10 degrees. A person skilled in the art can select a suitable instrument setting for analysis of particles of the present disclosure.

In embodiments of the present disclosure, guanidine-functionalized metal silicate particles have a surface nitrogen content in a range from 1 atomic percent to 20 atomic percent, as measured by XPS. In some embodiments, the guanidine-functionalized metal silicate particles have a surface nitrogen content of at least 1 atomic percent, at least 2, at least 3, at least 4, or even at least 5 atomic percent, as measured by XPS. In some embodiments, the guanidine-functionalized metal silicate particles have a surface nitrogen content of up to 20 atomic percent, up to 15, up to 10, up to 9, up to 8, up to 7, or even up to 6 atomic percent, as measured by XPS. The surface nitrogen content of the guanidine-functionalized metal silicate particles, as measured by XPS, may be any combination of these lower and upper values, inclusive of the values thereof. A person skilled in the art would understand that in some embodiments it may be preferred to select higher or lower surface nitrogen content within these ranges, depending on the desired application. Suitable guanidine-functionalized perlite particles for use according to the present disclosure include those that comprise perlite and that have a surface nitrogen content of greater than 2 and less than or equal to about 12, as determined by XPS. Suitable guanidine-functionalized diatomaceous earth particles for use according to the present disclosure include those that comprise diatomaceous earth and have a surface composition having surface nitrogen content of greater than 2 and less than or equal to about 12.

In some embodiments, particularly preferred are guanidine-functionalized magnesium silicate particles. Suitable guanidine-functionalized magnesium silicate particles for use according to the present disclosure include those that comprise an amorphous magnesium silicate and that have a surface composition having a metal atom to silicon atom ratio greater than 0.01 and less than or equal to about 0.5 (preferably, less than or equal to about 0.4; more preferably, less than or equal to about 0.3; most preferably, less than or equal to about 0.2), as determined by X-ray photoelectron spectroscopy ("XPS", also known as Electron Spectroscopy for Chemical Analysis ("ESCA")). In some embodiments, particularly preferred are guanidine-functionalized aluminum silicate particles. Suitable guanidine-functionalized aluminum silicate particles for use according to the present disclosure include those that comprise an amorphous aluminum silicate and that have a surface composition having a metal atom to silicon atom ratio greater than 6.7 and less than or equal to about 17.3, as determined by XPS (also known as ESCA). In some embodiments, particularly preferred are guanidine-functionalized perlite particles.

In an embodiment, the concentration agent particles comprise particles of diatomaceous earth, for instance particles of surface-modified diatomaceous earth. Diatomaceous earth (or kieselguhr) is a natural siliceous material produced from the remnants of diatoms, a class of ocean-dwelling microorganisms. Thus, it can be obtained from natural sources and is also commercially available (for example, from Alfa Aesar, A Johnson Matthey Company, Ward Hill, Mass.). Diatomaceous earth particles generally comprise small, open networks of silica in the form of symmetrical cubes, cylinders, spheres, plates, rectangular boxes, and the like. The pore structures in these particles can generally be remarkably uniform.

Diatomaceous earth can be used in carrying out the process of the invention as the raw, mined material or as purified and optionally milled particles. Preferably, the diatomaceous earth is in the form of milled particles with sizes in the range of about 1 micrometer to about 50 micrometers in diameter (more preferably, about 3 micrometers to about 10 micrometers). The diatomaceous earth can optionally be heat treated prior to use to remove any vestiges of organic residues. If a heat treatment is used, it can be preferable that the heat treatment be at 500° C. or lower, as higher temperatures can produce undesirably high levels of crystalline silica.

Surface-modified diatomaceous earth comprises diatomaceous earth bearing, on at least a portion of its surface, a surface treatment comprising titanium dioxide, ferric oxide, fine-nanoscale gold or platinum, or a combination thereof. Useful surface modifiers include fine-nanoscale gold; fine-nanoscale platinum; fine-nanoscale gold in combination with at least one metal oxide (preferably, titanium dioxide, ferric oxide, or a combination thereof); titanium dioxide; titanium dioxide in combination with at least one other (that is, other than titanium dioxide) metal oxide; and the like; and combinations thereof. Preferred surface modifiers include fine-nanoscale gold; fine-nanoscale platinum; fine-nanoscale gold in combination with at least ferric oxide or titanium dioxide; titanium dioxide; titanium dioxide in combination with at least ferric oxide; and combinations thereof. Surface-modified diatomaceous earth can be made, for example, according to methods disclosed in commonly assigned International Publication No. WO 2009/046191 (Kshirsagar et al.).

In an embodiment, the concentration agent particles comprise particles of gamma-FeO(OH) (also known as lepidocrocite). Specific examples of such concentration agent particles are disclosed in commonly assigned International Publication No. WO2009/046183 (Kshirsagar et al.). Gamma-FeO(OH) particles have been found to be surprisingly more effective than other iron-containing concentration agent particles in capturing gram-negative bacteria, which can be of great concern in regard to human bacterial infections.

Gamma-FeO(OH) is known and can be chemically synthesized by known methods (for example, by oxidation of ferrous hydroxide at neutral or slightly acidic pHs, as described for purposes of magnetic tape production in U.S. Pat. No. 4,729,846 (Matsui et al.), the description of which is incorporated herein by reference). Gamma-FeO(OH) is also commercially available (for example, from Alfa Aesar, A Johnson Matthey Company, Ward Hill, Mass., and from Sigma-Aldrich Corporation, St. Louis, Mo.).

In an embodiment, the concentration agent particles comprise particles of silica. A specific example of concentration agent silica particles is silicon dioxide microspheres having a mean diameter of about 2.5 microns that are commercially available from PolySciences, Inc., (Warrington, Pa.).

In an embodiment, the concentration agent particles comprise particles of metal carbonates. A specific example of concentration agent metal carbonate particles is calcium carbonate, such as calcium carbonate particles having a diameter range of 2.5-10 microns that are commercially available from Sigma-Aldrich, (St. Louis, Mo.).

In an embodiment, the concentration agent particles comprise particles of metal phosphates. A specific example of concentration agent metal phosphate particles is hydroxyapatite, such type-1 hydroxyapatite particles having particle sizes from 2-8 microns that are commercially available from Sigma-Aldrich, (St. Louis, Mo.) and BioRad (Hercules, Calif.).

In one specific method, the nonwoven article is prepared using a wet laying or "wetlaid" process. In this process, a dispersion is formed that contains (a) a plurality of fibers, (b) a plurality of concentration agent particles, (c) polymeric binder fibers (e.g., bi-component fibers), (d) and a dispersing liquid such as water, a water-miscible organic solvent, or a mixture thereof. The fibers and concentration agent particles can be dispersed together in the dispersing liquid. In some embodiments, the fibers (for example, hydrophobic fibers) have additives, surface treatments, or chemical groups that facilitate dispersion of the fibers in the dispersion liquid. For example, polyolefin-based fibers can have maleic anhydride or succinic anhydride functionality, or, during the melt-processing to prepare polyolefin-based fibers, a suitable surfactant can be added.

The wetlaid process additionally includes dewatering, followed by heating to finish the dewatering and optionally to bind some of the fibers together.

One or more adjuvants or additives are optionally used in preparing this type of nonwoven article. Useful adjuvants include process aids, surfactants, solvents, dispersants, flocculating aids, retention aids, or other materials that can enhance the overall performance of the resulting nonwoven article. When used, the amounts of such adjuvants can be present, for example, in an amount up 5 weight percent, up to 4 weight percent, up to 3 weight percent, up to 1 weight percent, or up to 0.5 weight percent based on a total dry weight of the nonwoven article (for example, fibers and concentration agent particles). The total amount of adjuvants is typically selected to be as low as possible so as to maximize the amount of concentration agent particles that can be included in the nonwoven article.

In one more specific wetlaid process, the fibers (for example, chopped fibers) can be blended in a container in the presence of the dispersing liquid (for example, water, a water-miscible organic solvent such as an alcohol, or a mixture thereof) to form a slurry. After formation of the slurry, the concentration agent particles and an optional precipitation agent (for example, a pH adjusting agent such as alum) can be added to the slurry.

When the wetlaid process is carried out by using handsheet methods known in the art, the order of addition of the components (i.e., fibers and concentration agent particles) to the dispersion has not been found to significantly affect the ultimate performance of the concentration device. After formation, the dispersion mixture can be poured into a mold, the bottom of which can be covered by a screen. The dispersing liquid can be allowed to drain from the mixture (in the form of a wet sheet) through the screen. After sufficient liquid has drained, the wet sheet generally can be removed from the mold and dried by pressing, heating, or a combination of the two. Generally pressures are in a range of about 300 to about 600 kPa. Temperatures in a range of 90° C. to 200° C., in a range of 100° C. to 175° C., in a range of 100° C. to 150° C., or in a range of 90° C. to 120° C. can be used for drying the wet sheet. Drying often removes all or most of the dispersing liquid (for example, up to 85 weight percent, up to 90 weight percent, up to 95 weight percent, up to 98 weight percent, or up to 99 weight percent of the dispersing liquid based on the amount of dispersing liquid added to form the dispersion).

The resulting nonwoven article is a dry sheet having an average thickness of at least 0.1 millimeter, at least 0.2 millimeters, at least 0.5 millimeters, at least 0.8 millimeters, at least 1 millimeter, at least 2 millimeters, at least 4 millimeters, or at least 5 millimeters. The average thickness is often up to 20 millimeters, up to 15 millimeters, up to 12 millimeters, or up to 10 millimeters. Calendering can be used to provide additional pressing or fusing, if desired, of the dry sheet. The basis weight of the nonwoven article (in the form of sheet material) can be in the range of about 100 to about 350 grams per square meter ($g/m^2$), preferably, in the range of about 200 to about 300 $g/m^2$, such as about 250 $g/m^2$.

In the nonwoven article, the concentration agent particles can be entrapped in the fibrous porous matrix through either chemical interactions (for example, chemical bonding) or physical interactions (for example, adsorption or mechanical entrapment), depending upon the nature of the fibers that are utilized. The concentration agent particles are often preferably distributed essentially uniformly throughout the fibrous porous matrix within the nonwoven article.

Generally the average pore size of the dry nonwoven article can be in a range of 0.1 to 10 micrometers, as measured by scanning electron microscopy (SEM). Void volumes in the range of 20 to 80 volume percent or in a range of 40 to 60 volume percent can be useful. The porosity of the dry nonwoven article can be modified (increased) by using fibers of larger diameter or stiffness in the fiber mixture.

Advantageously, nonwoven articles according to at least certain aspects of the present disclosure can be subjected to sterilization processes with minimal to no damage to the nonwoven articles. Suitable sterilization methods are known to the skilled practitioner, and include for instance and without limitation, steam treatment at a temperature of 121 degrees Celsius for at least 15 minutes, exposure to ethylene oxide, and gamma irradiation of the nonwoven articles.

Various embodiments are provided that include a device, a method, a kit, and a system.

Embodiment 1 is a device comprising a filter holder, the filter holder comprising a tip portion; a nonwoven article disposed on the tip portion of the filter holder; and an adaptor attached to the filter holder, the adaptor defining an aperture.

Embodiment 2 is the device of embodiment 1, wherein the adaptor further comprises at least one rib formed on an interior surface of the adaptor.

Embodiment 3 is the device of embodiment 1 or embodiment 2, wherein the filter holder and the adaptor are integrally formed.

Embodiment 4 is the device of embodiment 1 or embodiment 2, wherein the filter holder and the adaptor are detachable.

Embodiment 5 is the device of any of embodiments 1 to 4, wherein the filter holder and the adaptor are attached in series.

Embodiment 6 is the device of any of embodiments 1 to 4, wherein the device comprises a Y-shaped configuration.

Embodiment 7 is the device of embodiment 6, wherein the device further comprises a handle disposed in the filter holder and attached to the tip portion.

Embodiment 8 is the device of embodiment 6 or embodiment 7, wherein the device further comprises a housing configured to accept the Y-shaped configuration, wherein the housing comprises a waste collection container and a vent.

Embodiment 9 is the device of any of embodiments 1 to 8, wherein the nonwoven article is disposed on the tip portion distal from the adaptor.

Embodiment 10 is the device of any of embodiments 1 to 9, wherein the nonwoven article is configured to have a tube shape.

Embodiment 11 is the device of any of embodiments 1 to 10, wherein the filter holder comprises a tubular shape comprising a length and a width, wherein the length is at least three times greater than the width.

Embodiment 12 is the device of any of embodiments 1 to 11, wherein the adaptor comprises a volume of at least 10 milliliters.

Embodiment 13 is the device of any of embodiments 1 to 12, wherein the adaptor comprises a length of at least 35 millimeters.

Embodiment 14 is the device of any of embodiments 1 to 13, further comprising a cuvette, wherein the tip portion of the filter holder is configured to be inserted into the cuvette.

Embodiment 15 is the device of embodiment 14, further comprising at least one detection reagent disposed in the cuvette.

Embodiment 16 is the device of any of embodiments 1 to 15, wherein the filter holder further comprises a sleeve disposed in the filter holder.

Embodiment 17 is the device of embodiment 16, wherein the sleeve is slidably disposed in the filter holder.

Embodiment 18 is the device of any of embodiments 1 to 17, wherein the adaptor comprises an elastomeric portion that defines the aperture.

Embodiment 19 is the device of any of embodiments 1 to 18, wherein the nonwoven article comprises a fibrous porous matrix.

Embodiment 20 is the device of embodiment 19, wherein the nonwoven article further comprises a plurality of concentration agent particles enmeshed in the fibrous porous matrix.

Embodiment 21 is the device of embodiment 20, wherein the concentration agent particles comprise amorphous metal silicates, guanidine-functionalized metal silicates, diatomaceous earth, surface-modified diatomaceous earth, guanidine-functionalized diatomaceous earth, gamma-FeO(OH), metal carbonates, metal phosphates, silica, perlite, guanidine-functionalized perlite, or a combination thereof.

Embodiment 22 is the device of any of embodiments 19 to 21, wherein the fibrous porous matrix is a nonwoven fibrous layer comprising uncrimped polymeric fibers.

Embodiment 23 is the device of any of embodiments 1 to 22, further comprising a pressure differential source.

Embodiment 24 is the device of embodiment 23, wherein the pressure differential source comprises a syringe, a pump, or an aspirator.

Embodiment 25 is the device of any of embodiments 1 to 6 or 8 to 24, further comprising a handle configured to be inserted in the filter holder, the handle comprising a feature or mark disposed at a distance from an end of the handle.

Embodiment 26 is a method of detecting at least one microorganism strain or target cellular analyte in a fluid sample. The method comprises obtaining a device; placing a lumened or cannulated device in fluid communication with the device; and passing a fluid sample suspected of containing at least one microorganism strain or target cellular analyte from the lumened or cannulated device through the device and contacting the nonwoven article. The method further comprises contacting the nonwoven article with at least one detection reagent and detecting the presence of the at least one microorganism strain or target cellular analyte concentrated by the nonwoven article. The device comprises 1) a filter holder, the filter holder comprising a tip portion; 2) a nonwoven article disposed on the tip portion of the filter holder; and 3) an adaptor attached to the filter holder, the adaptor defining an aperture.

Embodiment 27 is the method of embodiment 26, wherein the fluid sample comprises a rinsate from the lumened or cannulated device.

Embodiment 28 is the method of embodiment 26 or embodiment 27, wherein prior to contacting the nonwoven article with the at least one detection reagent, the lumened or cannulated device is removed from being in fluid communication with the device and a handle is inserted into the filter holder and attached to the tip portion of the filter holder.

Embodiment 29 is the method of any of embodiments 26 to 28, wherein the contacting of the nonwoven article with the at least one detection reagent comprises an up-and-down or a back-and-forth motion of the nonwoven article with respect to the at least one detection reagent.

Embodiment 30 is the method of any of embodiments 26 to 29, wherein the contacting of the nonwoven article with the at least one detection reagent comprises vortexing the at least one detection reagent and the nonwoven article.

Embodiment 31 is the method of any of embodiments 26 to 30, wherein the contacting of the nonwoven article with the at least one detection reagent comprises manual agitation of the nonwoven article and the at least one detection reagent.

Embodiment 32 is the method of any of embodiments 26 to 31, wherein the fluid sample is passed through the device using a pressure differential.

Embodiment 33 is the method of embodiment 32, wherein the pressure differential is provided using a syringe, a pump, or an aspirator.

Embodiment 34 is the method of any of embodiments 26 to 33, wherein the pressure differential comprises positive pressure.

Embodiment 35 is the method of any of embodiments 26 to 33, wherein the pressure differential comprises negative pressure.

Embodiment 36 is the method of any of embodiments 26 to 35, wherein the lumened or cannulated device is placed in fluid communication with the device by inserting the lumened or cannulated device through the aperture of the adaptor, wherein at least 25 millimeters of a length of the lumened or cannulated device is disposed inside the adaptor.

Embodiment 37 is the method of any of embodiments 26 to 36, wherein the device further comprises a cuvette containing the at least one detection reagent, wherein the cuvette is inserted into a luminometer prior to detecting the presence of the at least one microorganism strain or target cellular analyte concentrated by the nonwoven article.

Embodiment 38 is the method of any of embodiments 26 to 37, wherein a difference in pressure of the fluid sample entering the device and exiting the device is no greater than 20 kilopascals.

Embodiment 39 is the method of any of embodiments 26 to 38, wherein the flow rate of the fluid sample through the device is at least 2 milliliters per minute and a difference in pressure of the fluid sample entering the device and exiting the device is no greater than 20 kilopascals.

Embodiment 40 is the method of any of embodiments 26 to 39, wherein the lumened or cannulated device comprises a medical device undergoing reprocessing.

Embodiment 41 is the method of any of embodiments 26 to 40, wherein the lumened or cannulated device comprises a flexible endoscope, a semi-rigid endoscope, a rigid endoscope, a laparoscopic instrument, or a cannulated robotic surgical instrument.

Embodiment 42 is a kit comprising a device; a cuvette containing at least one detection reagent; and a handle configured to be inserted into the filter holder. The device includes 1) a filter holder, the filter holder comprising a tip portion; 2) a nonwoven article disposed on the tip portion of the filter holder; and 3) an adaptor attached to the filter holder, the adaptor defining an aperture.

Embodiment 43 is the kit of embodiment 42, further comprising a stand configured to hold the device.

Embodiment 44 is the kit of embodiment 42 or embodiment 43, further comprising instructions for using the kit to detect at least one microorganism strain or target cellular analyte in a fluid sample.

Embodiment 45 is the kit of any of embodiments 42 to 44, further comprising a pressure differential source comprising a syringe, a pump, or an aspirator.

Embodiment 46 is a system comprising: a device; a cuvette containing at least one detection reagent; a handle configured to be inserted into the filter holder; and a luminometer. The device comprises 1) a filter holder, the filter holder comprising a tip portion; 2) a nonwoven article disposed on the tip portion of the filter holder; and 3) an adaptor attached to the filter holder, the adaptor defining an aperture.

Embodiment 47 is the system of embodiment 46, further comprising a lumened or cannulated device.

Embodiment 48 is the system of embodiment 46 or embodiment 47, further comprising instructions for using the system to detect at least one microorganism strain or target cellular analyte in a fluid sample.

Embodiment 49 is the system of any of embodiments 46 to 48, further comprising a stand configured to hold the device.

Embodiment 50 is the system of any of embodiments 46 to 49, further comprising a pressure differential source comprising a syringe, a pump, or an aspirator.

Embodiment 51 is a method of detecting at least one microorganism strain or target cellular analyte in a fluid sample. The method comprises obtaining a device comprising a Y-shaped configuration. The method further comprises placing a lumened or cannulated device in fluid communication with the device; and passing a fluid sample suspected of containing at least one microorganism strain or target cellular analyte from the lumened or cannulated device through the device and contacting the nonwoven article. The method additionally comprises contacting the nonwoven article with at least one detection reagent and detecting the presence of the at least one microorganism strain or target cellular analyte concentrated by the nonwoven article. The device comprises 1) a filter holder, the filter holder comprising a tip portion; 2) a nonwoven article disposed on the tip portion of the filter holder; 3) a container configured to hold the filter holder; and 4) an adaptor attached to the container in a Y-shaped configuration, the adaptor defining an aperture.

Embodiment 52 is the method of embodiment 51, wherein the fluid sample comprises a rinsate from the lumened or cannulated device.

Embodiment 53 is the method of embodiment 51 or embodiment 52, wherein the device further comprises a handle integrally attached to the filter holder.

Embodiment 54 is the method of any of embodiments 51 to 53, wherein the contacting of the nonwoven article with the at least one detection reagent comprises an up-and-down or a back-and-forth motion of the nonwoven article with respect to the at least one detection reagent.

Embodiment 55 is the method of any of embodiments 51 to 54, wherein the contacting of the nonwoven article with the at least one detection reagent comprises vortexing the at least one detection reagent and the nonwoven article.

Embodiment 56 is the method of any of embodiments 51 to 55, wherein the contacting of the nonwoven article with the at least one detection reagent comprises manual agitation of the nonwoven article and the at least one detection reagent.

Embodiment 57 is the method of any of embodiments 51 to 56, wherein the fluid sample is passed through the device using a pressure differential.

Embodiment 58 is the method of embodiment 57, wherein the pressure differential is provided using a syringe, a pump, or an aspirator.

Embodiment 59 is the method of any of embodiments 51 to 58, wherein the pressure differential comprises positive pressure.

Embodiment 60 is the method of any of embodiments 51 to 58, wherein the pressure differential comprises negative pressure.

Embodiment 61 is the method of any of embodiments 51 to 60, wherein the lumened or cannulated device is placed in fluid communication with the device by inserting the lumened or cannulated device through the aperture of the adaptor, wherein at least 25 millimeters of a length of the lumened or cannulated device is disposed inside the adaptor.

Embodiment 62 is the method of any of embodiments 51 to 61, further comprising inserting the filter holder into a cuvette containing the at least one detection reagent, wherein the cuvette is inserted into a luminometer prior to detecting the presence of the at least one microorganism strain or target cellular analyte concentrated by the nonwoven article.

Embodiment 63 is the method of any of embodiments 51 to 62, wherein a difference in pressure of the fluid sample entering the device and exiting the device is no greater than 20 kilopascals.

Embodiment 64 is the method of any of embodiments 51 to 63, wherein the flow rate of the fluid sample through the device is at least 2 milliliters per minute and a difference in pressure of the fluid sample entering the device and exiting the device is no greater than 20 kilopascals.

Embodiment 65 is the method of any of embodiments 51 to 64, wherein the lumened or cannulated device comprises a medical device undergoing reprocessing.

Embodiment 66 is the method of any of embodiments 51 to 65, wherein the lumened or cannulated device comprises a flexible endoscope, a semi-rigid endoscope, a rigid endoscope, a laparoscopic instrument, or a cannulated robotic surgical instrument.

Embodiment 67 is the method of any of embodiments 51 to 66, wherein the device further comprises a housing configured to hold each of the filter holder and the adaptor.

Embodiment 68 is a kit comprising a device comprising a Y-shaped configuration; a cuvette containing at least one detection reagent; and a handle configured to be inserted into the filter holder. The device comprises 1) a filter holder, the filter holder comprising a tip portion; 2) a nonwoven article disposed on the tip portion of the filter holder; 3) a container configured to hold the filter holder; and 4) an adaptor attached to the container in a Y-shaped configuration, the adaptor defining an aperture.

Embodiment 69 is the kit of embodiment 68, further comprising a housing configured to hold each of the filter holder and the adaptor.

Embodiment 70 is the kit of embodiment 68 or embodiment 69, further comprising instructions for using the kit to detect at least one microorganism strain or target cellular analyte in a fluid sample.

Embodiment 71 is the kit of any of embodiments 68 to 70, further comprising a pressure differential source comprising a syringe, a pump, or an aspirator.

Embodiment 72 is a system comprising: a device comprising a Y-shaped configuration; a cuvette containing at least one detection reagent; a handle configured to be inserted into the filter holder; and a luminometer. The device comprises 1) a filter holder, the filter holder comprising a tip portion; 2) a nonwoven article disposed on the tip portion of the filter holder; 3) a container configured to hold the filter holder; and 4) an adaptor attached to the container in a Y-shaped configuration, the adaptor defining an aperture.

Embodiment 73 is the system of embodiment 72, further comprising a lumened or cannulated device.

Embodiment 74 is the system of embodiment 72 or embodiment 73, further comprising instructions for using the system to detect at least one microorganism strain or target cellular analyte in a fluid sample.

Embodiment 75 is the system of any of embodiments 72 to 74, further comprising a housing configured to hold each of the filter holder and the adaptor.

Embodiment 76 is the system of any of embodiments 72 to 75, further comprising a pressure differential source comprising a syringe, a pump, or an aspirator.

EXAMPLES

Unless otherwise noted, all chemicals used in the examples can be obtained from Sigma-Aldrich Corp. (Saint Louis, Mo.). Unless otherwise specified, all microbiological supplies and reagents were purchased as standard products from either Sigma-Aldrich or VWR.

| Material | Vendor |
| --- | --- |
| Fiber 1 - SHORT STUFF E380F ~0.7 mm average length, 15 microns diameter polyethylene fibers | MiniFIBERS, Inc.; Johnson City, TN |
| Fiber 2 - 6 denier 2 inches long chopped nylon fibers | MiniFIBERS, Inc.; Johnson City, TN |
| Fiber 3 - 1 denier bi-component ethylene vinyl acetate/ polypropylene fibers | MiniFIBERS, Inc.; Johnson City, TN |
| Fiber 4 - long glass fibers (MICRO-STRAND 106-475 Glass Fiberglas) Schuller Inc. | Johns Mansville; Denver, CO |
| Fiber 5 - 0.06 denier, 2.5 microns diameter, 1.5 mm in length polyester/ copolyester fibers | Cyphrex 10001 fibers from Eastman Co., Kingsport, TN |
| Fiber 6 - 2 denier 5 mm bi-component copolyester fibers made of polyester as the core and PET as the sheath | MiniFIBERS, Inc.; Johnson City, TN |
| Fiber 7 - typical length 4.3 mm (range 4.5-7.5 mms), specific gravity 1.17 acrylonitrile fibers | CFF Fibrillated Fiber 114-3 from Sterling Fibers, Inc. Pace, FL |
| CM-111 - Amorphous spheroidized magnesium silicate: Cosmetic Microspheres (CM-111) | 3M Company; St. Paul, MN |
| G-CM-111 Guanylated CM-111 made according to the method of Example E1-D in PCT/US2014/040861 | 3M Company; St. Paul, MN |
| G-Perlite Guanylated Perlite made according to copending U.S. Ser. No. 62/135,303 (Docket 76251US002) | 3M Company; St. Paul, MN |
| DI Water - Deionized filtered 18 megaohm water from a Milli-Q Gradient System | Millipore; Waltham, MA |
| ATP free water - HYPURE Molecular biology grade water, Catalog # SH30538.02 | Thermo Fisher Scientific; Waltham, MA |
| CLEAN-TRACE lysis reagent - reagent for bioluminescence assay | 3M Company; Bridgend, UK |
| CLEAN-TRACE luciferin-luciferase enzyme reagent - reagent for bioluminescence assay | 3M Company; Bridgend, UK |
| Tryptic Soy Broth - DIFCO Tryptic Soy Broth, prepared at 3% according to the manufacturer's instructions | Becton Dickenson; Sparks MD |
| E. coli plate - 3M E coli/Colifom PETRIFILM Plate; | 3M Company; St. Paul MN |
| PAC - 3M PETRIFILM Aerobic Count Plates | 3M Company; St. Paul MN |
| BBL Buffer - Butterfield's buffer, pH 7.2 ± 0.2, monobasic potassium phosphate buffer solution (VWR Catalog Number 83008-093) | VWR; West Chester, PA |
| 3M CLEAN-TRACE NG luminometer | 3M Company, Bridgend, UK |
| Cuvettes - Greiner Bio-One polystyrene 4 mL tubes | VWR; West Chester, PA |
| Microfuge tubes - 1.5 mL BrandTech polypropylene tubes | VWR; West Chester, PA |
| 80-6116-0326-9 3M Heat Shrink Thin-Wall Flexible Polyolefin Adhesive-Lined Tubing | 3M Company; St. Paul MN |

-continued

| Material | Vendor |
| --- | --- |
| Phosphate buffered water | Sigma Aldrich; St. Louis, MO |
| ATP (adenosine triphosphate) | Sigma Aldrich; St. Louis, MO |
| Sterile water | Baxter; Deerfield, IL |
| Whole Sheep Blood | Thermo Fisher Scientific; Waltham, MA |
| UX-95802-12 Platinum-Cured Silicone tubing | Cole Palmer; Vernon Hills, IL |
| 3M CLEAN-TRACE Water Test | 3M Company; St. Paul MN |
| Sterile 60 cc syringes | Becton Dickenson; Sparks MD |

Preparation of Nonwoven Fibrous Porous Matrices Containing Calcined Magnesium Silicate Examples 1, 2 and 3

Three fiber premixes were prepared by mixing various amounts of Fiber 1, Fiber 2, Fiber 3, and Fiber 4 as shown in Table 1 below. The fibers were added to 3 liters of cold deionized water in a 4 L blender (available from VWR, Radnor, Pa., under the trade designation "WARING COMMERCIAL HEAVY DUTY BLENDER, MODEL 37BL84") and blended at low speed for 30 seconds. The mixture was examined for uniform dispersion of the fibers without nits or clumps. The additive particles, CM-111, were added with an additional liter of deionized water and mixed at low speed for 15 seconds.

A nonwoven fibrous porous felt was prepared using a pad maker apparatus (obtained from Williams Apparatus, Watertown, N.Y., under the trade designation "TAPPI") that had a box measuring about 30 centimeters (12 inches) square and 30 centimeters (~12 inches) high with a fine mesh screen at the bottom and a drain valve. On the screen ~a 14 inch (36 cm)×12 inch (30 cm) piece of a polyethylene spunbond (PET Lutradur 7240 obtained from Fiberweb, Cincinnati, Ohio) was laid as scrim on the screen. The box was filled with tap water up to a height of about 1 centimeter above the screen. Each fiber and particle mixture was poured into the box and the valve was opened immediately which created a vacuum that pulled the water out of the box.

The fibrous nonwoven felts were each transferred from the apparatus onto a 20 centimeter square sheet of blotter paper (96-pound white paper, obtained from Anchor Paper, St. Paul, Minn.). Each felt was sandwiched between 2 to 4 layers of blotter paper, to blot excess water. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 3 hours to remove residual water and to form a nonwoven fibrous porous matrix. The resulting fibrous porous matrices of Examples 1 and 2 were approximately 0.8-1 millimeter thick. The fibrous porous matrix of Example 3 was approximately 0.8-0.9 millimeter thick.

FIGS. 1-3 are scanning electron microscope (SEM) images of the exemplary nonwoven articles of Examples 1-3, respectively.

TABLE 1

Compositions of Examples 1-3

| Materials (in grams) | Example 1 | Example 2 | Example 3 |
|---|---|---|---|
| Fiber 1 | 11.08 | 10.98 | 8.83 |
| Fiber 2 | 3.01 | 0 | 2.44 |
| Fiber 3 | 2.30 | 2.29 | 1.82 |
| Fiber 4 | 0 | 1.8 | 1.4 |
| CM-111 | 5.15 | 5.07 | 5.03 |
| Basis weight (g/m$^2$) | 196.66 | 203.44 | 197.74 |

Preparation of Nonwoven Fibrous Porous Matrices Containing Guanylated Magnesium Silicate Examples 4, 5, 6, 7 and 8

Nonwoven fibrous porous matrices of Examples 4, 5, 6, 7, and 8 were made using the procedure described above. The formulations are shown in Table 2 below.

TABLE 2

Compositions of Examples 4-8

| Materials (in grams) | Example 4 | Example 5 | Example 6 | Example 7 | Example 8 |
|---|---|---|---|---|---|
| Fiber 1 | 11.03 | 11.05 | 11.08 | 11.05 | 11.01 |
| Fiber 2 | 0 | 0 | 3.02 | 3.03 | 3.01 |
| Fiber 3 | 2.25 | 2.26 | 2.27 | 2.25 | 2.26 |
| Fiber 4 | 2.25 | 0 | 1.76 | 0 | 1.76 |
| Guanylated CM-111 | 5.00 | 5.00 | 5.01 | 5.00 | 5.00 |
| Basis weight (g/m$^2$) | 217.07 | 166.30 | 238.32 | 199.02 | 229.82 |

The thickness of the fibrous porous matrices of Example 4 was approximately 0.8-0.9 mm, Example 5 was approximately 0.6-0.8 mm thick, and Examples 6-8 were each approximately 0.8-1.0 mm thick.

Example 9: Bacteria Used in Example 11

The various bacteria used in Example 11 (see Table 3 below) were obtained from ATCC (Manassas, Va.).

TABLE 3

Bacteria used in Example 11

| Bacteria | ATCC No. |
|---|---|
| Escherichia coli | 51813 |
| Staphylococcus aureus | 6538 |
| Enterobacter aerogenes | 29007 |
| Pseudomonas aeruginosa | 9027 |

Pure cultures of the bacterial strains were inoculated into Tryptic Soy Broth (TSB, Becton, Dickinson and Company, Franklin Lakes, N.J.) and were grown overnight at 37° C. The cultures were diluted serially in Butterfield phosphate buffer (3M Co., St. Paul, Minn.) to obtain desired amount of colony forming units (cfu) per ml for spiking into water samples. *E. coli* and *E. aerogenes* were quantified by plating appropriate dilutions on 3M PETRIFILM *E. coli*/Coliform Count Plates (3M Company) according to manufacturer's instructions and incubated overnight at 37° C. *S. aureus* and *P. aeruginosa* were quantified by plating appropriate dilutions on 3M PETRIFILM aerobic count plates (3M Company) and incubated overnight at 37° C. The plates were read using 3M PETRIFILM Plate Reader (3M Co.) and colony forming units (cfu) were determined.

Example 11: Detection of Bacteria in Nonwoven Fibrous Porous Matrices by ATP Bioluminescence Each nonwoven fibrous porous matrix containing bound bacteria was removed from the SWINNEX filter holder and transferred aseptically to a 1.5 ml microfuge tube (Plastibrand microtubes, Brand GmbH & Co. KG, Wertheim, Germany). 200 microliters of CLEAN-TRACE lysis reagent) containing bacterial lysis reagent was added to the tube and vortexed for 1 minute and allowed to sit at room temperature for additional 1 minute. 250 microliters of CLEAN-TRACE luciferin-luciferase enzyme reagent) was added to the tube and mixed. The tube was placed immediately into a bench-top luminometer (20/20n single tube luminometer, Turner Biosystems, Sunnyvale, Calif.) and measurement of RLUs was recorded. The luminescence measurements were obtained from the luminometer using spreadsheet interface PC software that was provided with the luminometer. 100 microliters of buffer containing 10,000 cfu of bacteria was pipetted into a 1.5 ml microfuge tube (Plastibrand microtubes) and upon addition of lysis mix (200 microliters) and ATP reagent (250 microliters), luminescence was measured. The relative light units obtained from 10,000 cfu was used to calculate the percent recovery of ATP in nonwoven fibrous porous matrices (see Tables 4 and 5 below). The ATP recovery varied from 30 to 68% with uncut material and the matrix without Fiber 2 gave the most recovery (60 to 68%).

TABLE 4

Bacterial capture efficiency and percent recovery of ATP in uncut nonwoven fibrous porous matrices containing calcined magnesium silicate

| | EC_10,000 cfu total | | SA_10,000 cfu total | |
|---|---|---|---|---|
| Matrix | % Capture | % ATP Recovery | % Capture | % ATP Recovery |
| Example 1 | 60 | 32 | 32 | 30 |
| Example 2 | 94 | 62 | 92 | 60 |
| Example 3 | 77 | 48 | 85 | 45 |

| | EA_10,000 cfu total | | PA_10,000 cfu total | |
|---|---|---|---|---|
| Matrix | % Capture | % ATP Recovery | % Capture | % ATP Recovery |
| Example 1 | 48 | 35 | 38 | 30 |
| Example 2 | 95 | 55 | 90 | 58 |
| Example 3 | 65 | 35 | 62 | 30 |

TABLE 5

Bacterial capture efficiency and percent recovery of ATP in uncut nonwoven fibrous porous matrices containing guanylated magnesium silicate

| | EC_10,000 cfu total | | SA_10,000 cfu total | |
|---|---|---|---|---|
| Matrix | % Capture | % ATP Recovery | % Capture | % ATP Recovery |
| Example 4 | 60 | 56 | 70 | 55 |
| Example 5 | 93 | 65 | 95 | 68 |
| Example 6 | 85 | 46 | 91 | 49 |

In another experiment, the nonwoven fibrous porous matrix was aseptically cut into small pieces and then transferred to 1.5 ml microfuge tube (Plastibrand microtubes). 200 microliters of the lysis mix containing bacterial lysis reagent was added to the tube and vortexed for 1 minute and allowed to sit at room temperature for an additional 1 minute. 250 microliters of the ATP reagent containing luciferin and luciferase was added to the tube and mixed. The luminescence was measured as described above. The percent recovery of ATP in nonwoven fibrous porous matrices is shown in Tables 6 and 7 below. The ATP recovery varied from 55 to 77% with uncut material mid the wet-laid without Fiber 2 gave the most recovery (70 to 77%)

TABLE 6

Bacterial capture efficiency and percent recovery of ATP in cut fibrous porous matrices containing calcined magnesium silicate

| | EC_10,000 cfu total | | SA_10,000 cfu total | |
|---|---|---|---|---|
| Matrix | % Capture | % ATP Recovery | % Capture | % ATP Recovery |
| Example 1 | 55 | 60 | 45 | 55 |
| Example 2 | 92 | 77 | 90 | 70 |
| Example 3 | 75 | 65 | 82 | 72 |

| | EA_10,000 cfu total | | PA_10,000 cfu total | |
|---|---|---|---|---|
| Matrix | % Capture | % ATP Recovery | % Capture | % ATP Recovery |
| Example 1 | 45 | 55 | 35 | 40 |
| Example 2 | 90 | 68 | 90 | 65 |
| Example 3 | 68 | 52 | 65 | 55 |

TABLE 7

Bacterial capture efficiency and percent recovery of ATP in cut fibrous porous matrices containing guanylate magnesium silicate

| | EC_10,000 cfu total | | SA_10,000 cfu total | |
|---|---|---|---|---|
| Matrix | % Capture | % ATP Recovery | % Capture | % ATP Recovery |
| Example 4 | 62 | 55 | 68 | 57 |
| Example 5 | 91 | 68 | 90 | 70 |
| Example 6 | 83 | 52 | 88 | 45 |

Examples 12-14: Making Nonwoven Fibrous Porous Matrices with Calcined Magnesium Silicate Three fiber premixes were prepared by mixing various amounts of Fiber 1, Fiber 2, Fiber 4, Fiber 5 and Fiber 6 as shown in Table 8 below.

For Example 12, the fibers were added to 3 liters of cold deionized water in a 4 L blender (available from VWR, Radnor, Pa., under the trade designation "WARING COMMERCIAL HEAVY DUTY BLENDER, MODEL 37BL84") and blended at low speed for 30 seconds. The mixture was examined for uniform dispersion of the fibers without nits or clumps. The additive particles, CM-111, were added with an additional liter of deionized water and mixed at low speed for 15 seconds.

For Examples 13 and 14, Fiber 5 was blended in 3 liters of cold deionized water for 30 seconds at medium speed. All other fibers were added and blended for 30 seconds at low speed.

The additive particles, CM-111, were added with an additional liter of deionized water and mixed at low speed for 15 seconds.

A nonwoven fibrous porous felt was prepared using a pad maker apparatus (obtained from Williams Apparatus, Watertown, N.Y., under the trade designation "TAPPI") that had a box measuring about 30 centimeters (12 inches) square and 30 centimeters (12 inches) high with a fine mesh screen at the bottom and a drain valve. On the screen ~a 14 inch (36 cm)×12 inch (30 cm) piece of a polyethylene spunbond (PET Lutradur 7240 obtained from Fiberweb, Cincinnati, Ohio) was laid as scrim on the screen. The box was filled with tap water up to a height of about 1 centimeter above the screen. Each fiber and additive mixture was poured into the box and the valve was opened immediately which created a vacuum that pulled the water out of the box.

The fibrous nonwoven felts were transferred from the apparatus onto a 20 centimeter square sheet of blotter paper (96-pound white paper, obtained from Anchor Paper, St. Paul, Minn.). Each felt was sandwiched between 2 to 4 layers of blotter paper, to blot excess water. The pressed felt of Example 12 was then transferred onto a fresh sheet of blotter paper and placed in an oven (HERATHERM oven series OMS100 obtained from Thermo Fisher Scientific, Waltham, Mass.) set at 130° C. for about 3 hours to remove residual water and to form a nonwoven fibrous porous matrix. The felts of Examples 13 and 14 were dried at 125° C. for about 3 hours to remove residual water and to form a nonwoven fibrous porous matrix. The resulting fibrous porous matrices of Examples 12 and 14 were approximately 1.30 to 1.40 millimeters thick. The fibrous porous matrix of Example 13 was 1.45-1.55 millimeters thick.

TABLE 8

Compositions of Examples 12-14

| Material (grams) | Example 12 | Example 13 | Example 14 |
|---|---|---|---|
| Fiber 1 | 11.00 | 7.74 | 7.70 |
| Fiber 2 | 3.00 | 3.06 | 3.0 |
| Fiber 4 | 1.75 | 1.78 | 1.75 |
| Fiber 5 | 0 | 8.06 | 0 |
| Fiber 6 | 2.25 | 2.28 | 2.30 |
| Fiber 7 | 0 | 0 | 11.78 |
| CM-111 | 10.00 | 10.00 | 10.01 |
| Basis weight (g/m$^2$) | 275.02 | 261.89 | 276.20 |

Testing of Nonwoven Fibrous Porous Matrices with Metal Silicate for Bacterial Capture of *E. coli*

A single colony from a streak culture of *E. coli* (ATCC 11229, a Gram negative organism) was inoculated into 10 ml of TSB (Tryptic Soy Broth, 3% by weight from Difco) incubated overnight for about 20 hours at 37 degrees C. The resulting bacterial stock contained about 1×10$^9$ cfus/ml. That stock was serially diluted in deionized water to make a working stock of 1×10$^2$ cfus/ml.

Examples 15-17

14 mm disks of nonwoven fibrous porous matrix of Example 12-14, respectively, were each die punched and inserted into 13 mm filter holders (Swinnex holders obtained from Millipore). Ten ml of the above working stock was filtered through the disk using a 10 cc syringe. After filtration the disks were discarded. The filtrates were collected in sterile 15 ml polypropylene tubes. A one ml volume of each filtrate was plated on PAC plates and tested for *E. coli* capture.

The stock solution was also plated on PAC. This was the "100% control". Plate counts were measured per manufacturer's instructions using a PETRIFILM Plate Reader. Capture efficiency was calculated using the formulas below. The results are shown in Table 19.

% Control=(CFUs in plated filtrates)×100/CFUs in 100% Control

% Capture Efficiency=100−% Control

TABLE 9

Capture of *E. coli*

| Sample | Example 15 | Example 16 | Example 17 |
|---|---|---|---|
| % Capture Efficiency | 71.7 (13) | 52.7 (11) | 95.1 | n = 3, % std deviation less than 10% unless otherwise noted in parentheses. The plated 100% control had an average of 163.5 cfus/ml (26% stdev, total 1635 cfus in 10 ml).

Testing of Nonwoven Fibrous Porous Matrices with Metal Silicate for Bacterial Capture of *S. aureus*

A single colony from a streak culture of *S. aureus* (ATCC 6538, a Gram positive organism) was inoculated into 10 ml of TSB (Tryptic Soy Broth, 3% by weight from Difco) incubated overnight for about 20 hours at 37 degrees C. The resulting bacterial stock contained about $1 \times 10^9$ cfus/ml. That stock was serially diluted in deionized water to make a working stock of $1 \times 10^2$ cfus/ml.

Examples 18-20

14 mm disks of nonwoven fibrous porous matrix of each of Examples 12-14, respectively, were die punched and inserted into 13 mm filter holders (Swinnex holders obtained from Millipore). Ten ml of above working stock was filtered through the disk using a 10 cc syringe. After filtration the disks were discarded. The filtrates were collected in sterile 15 ml polypropylene tubes. A one ml volume of each filtrate was plated on PAC plates. Each disk was tested for *S. aureus* capture.

The stock solution was also plated on PAC. This was the "100% control". Plate counts were measured per manufacturer's instructions using a PETRIFILM Plate Reader. Capture efficiency was calculated using the formulas below. The results are shown in Table 20.

% Control=(CFUs in plated filtrates)×100/CFUs in 100% Control

% Capture Efficiency=100−% Control

TABLE 10

Capture of *S. aureus*

| Sample | Example 18 | Example 19 | Example 20 |
|---|---|---|---|
| % Capture Efficiency | 99.36 | 100 | 99.36 | n = 3, % std deviation less than 10% unless otherwise noted in parentheses. The plated 100% control had an average 156 cfus/ml (total 1566 cfus in 10 ml).

Filter Holder Assembly Preparation

Preparation of a filter holder assembly as depicted in FIG. 1B began with forming a sock (106 in FIG. 1B) from a given nonwoven article (Examples 21-23 prepared according to the procedure of Examples 12-14 and having the compositions shown in Table 11 below), using either ultrasonication or heat welding. An individual sock was then slipped onto the tip portion (104 in FIG. 1B) of a custom injection molded filter holder part (102 in FIG. 1B). The nonwoven article sock was then secured to the plastic tip portion using a short piece of heat shrink tubing (105 in FIG. 1B, available from 3M, St. Paul).

Bacteria Sample Preparation

A stock bacterial suspension was prepared in Phosphate Buffered Water (PBW) (available from Sigma-Aldrich) at a concentration of ~$10^8$ CFUs/mL from a growth plate according to ASTM-E2315 method. To enumerate and verify the suspension's initial bacterial concentration, $10^{-6}$ and $10^{-7}$ dilutions of the prepared suspension were plated on PETRIFILM AC (available from 3M, St. Paul, Minn.) and incubated overnight at 37 degrees Celsius for enumeration. Dilutions for testing were prepared by diluting the stock bacterial suspension in MilliQ water.

Adenosine TriPhosphate (ATP) Sample Preparation

An ATP (available from Sigma-Aldrich) challenge solution was prepared in sterile water (available from Baxter). Challenge solutions used had concentrations of 5, 10, 100, 500, 1000 and 5000 femtomoles/mL.

Blood Sample Preparation

A blood challenge solution was prepared by diluting in saline a whole sheep blood sample (available from Fisher Scientific) 5-fold yielding a $10^{-5}$ diluted blood solution.

Testing Procedure

A sterile 60 cc syringe (available from BD, East Rutherford, N.J.) was filled with 40 mL of a given sample as prepared above, and subsequently connected to a piece of silicone tubing (available from Cole-Parmer) simulating the presence of an endoscope. A filter holder assembly as depicted in FIG. 4 and prepared as described above, was connected to the other end of the silicon tubing. The bacterial suspension was pushed through the filter holder (including through the tip portion and the nonwoven article sock) using the syringe at a rate of approximately 80 mL/minute. Once all the bacterial sample was pushed through the filter holder, the syringe was disconnected, refilled with 60 cc of air, and reconnected to the silicone tubing. The air was then pushed through the tubing and filter holder to make sure that any remaining liquid sample in the connected assembly was passed through the filter holder. The filter holder was then disconnected from the silicone tubing and introduced into a modified 3M Clean Trace Water Test (available from 3M, St. Paul, Minn.) as depicted in FIG. 5. The 3M Clean Trace Water Test was modified from the commercially available version by placing 135 μL of CLEAN-TRACE lysis reagent into a double film sealed pot (127 in FIG. 5). Using the handle (118 in FIG. 5) connected to the filter holder (102 in FIG. 4), the tip portion including the nonwoven article sock was pushed in and out of the cuvette (112 in FIG. 5) containing the Luciferin/Luciferase enzyme reagents used to detect total ATP, a total of five times. The 3M Clean Trace Water Test tube was then placed into a 3M NGi Luminometer (available from 3M, St. Paul, Minn.) to measure the amount of ATP present in the sample collected in the filter tip, in terms of Relative Light Units (RLUs).

Comparative examples were performed testing the same samples using the unmodified 3M Clean Trace Water Test according to the manufacturer's instructions, without concentrating the samples prior to ATP testing.

Effects of various agitation (e.g., contacting) methods were evaluated by repeating the test using the nonwoven article of Example 21 with $10^5$ CFUs/mL *S. aureus* bacteria and varying the specific agitation method of the nonwoven article with respect to the Luciferin/Luciferase enzyme reagents. The agitation methods tested included 10 seconds of manual agitation (e.g., shaking), 10 seconds of vortexing, 30 seconds of vortexing, and drawing the filter holder handle attached to the nonwoven article up and down three times.

Test Results for Examples 21-23

TABLE 11

Multiple Analyte Detection

| Example | Non-Woven Composition (% by weight) | | | | | | |
|---|---|---|---|---|---|---|---|
| | Fiber 1 | Fiber 2 | Fiber 3 | Fiber 4 | Fiber 6 | Fiber 7 | CM-111 |
| 21 | 40 | 11 | 8 | 6 | — | — | 35 |
| 22 | 40 | 11 | — | 6 | 8 | — | 35 |
| 23 | 33 | 11 | — | 6 | 8 | 5 | 35 |

| Example | Detection (RLUs) | | | | |
|---|---|---|---|---|---|
| | Background (no analyte) | ATP (10 femtomoles per mL) | Bacteria (*E. coli* ATCC 11229 @$10^4$ CFUs/mL) | Bacteria (*S. aureus* ATCC 6530 @$10^4$ CFUs/mL) | Blood ($10^{-5}$ dilution in saline) |
| 21A | 29 ± 3 | 113 ± 9 | 71 ± 9 | 215 ± 40 | 899 ± 125 |
| 22A | 38 ± 1 | 122 ± 12 | 91 ± 10 | 226 ± 49 | 1037 ± 132 |
| 23A | 32 ± 2 | 191 ± 15 | 73 ± 5 | 282 ± 91 | 716 ± 75 |

All values are the mean of at least 10 replicates. All errors are ±one standard error of the mean.

TABLE 12

Linearity in ATP Detection

| Example | Non-Woven Composition (% by weight) | | | | | | |
|---|---|---|---|---|---|---|---|
| | Fiber 1 | Fiber 2 | Fiber 3 | Fiber 4 | Fiber 6 | Fiber 7 | CM-111 |
| 21 | 40 | 11 | 8 | 6 | — | — | 35 |

| Example | ATP Concentration (femtomoles/mL) | Detection Signal (RLUs) |
|---|---|---|
| 21B | 0 | 17 ± 1 |
| 21C | 5 | 82 ± 8 |
| 21D | 10 | 173 ± 18 |
| 21E | 100 | 1449 ± 136 |
| 21F | 500 | 5955 ± 854 |
| 21G | 1000 | 14071 ± 1451 |

All values are the mean of at least 5 replicates. All errors are ±one standard error of the mean.

TABLE 13

Improvement in Sensitivity Over Unconcentrated Samples

| Example | Non-Woven Composition (% by weight) | | | | | | |
|---|---|---|---|---|---|---|---|
| | Fiber 1 | Fiber 2 | Fiber 3 | Fiber 4 | Fiber 6 | Fiber 7 | CM-111 |
| 21 | 40 | 11 | 8 | 6 | — | — | 35 |

| Example | Analyte Sample | Limit of Detection for Assay using Non-woven (Example 21) | Limit of Detection without Concentration | Sensitivity Improvement |
|---|---|---|---|---|
| 21H | ATP | 9 femtomole/mL | 49 femtomole/mL | 5.5x |
| 21I | *S. aureus* ATCCC 6530 | 24,099 CFUs/mL | 378,443 CFUs/mL | 15.7x |
| 21J | *E. coli* ATCCC 11229 | 72,277 CFUs/mL | 119,399 CFUs/mL | 1.7x |
| 21K | Blood | $10^{-5.6}$ | $10^{-5}$ | 4x |

Sensitivity analysis was performed for a selected false positive and false negative rate of 1%.

TABLE 14

Comparison of Agitation Methods

| Example | Agitation Method | Detection of *S. aureus* ATCC 6530 Bacteria @$10^5$ CFUs/mL (RLUs) |
|---|---|---|
| 21L | 10 seconds manual agitation | 86 ± 10 |
| 21M | 10 seconds vortexing | 129 ± 17 |
| 21N | 30 seconds vortexing | 292 ± 27 |
| 21O | 3 times up and down | 1062 ± 101 |

All values are the mean of at least 10 replicates. All errors are ±one standard error of the mean.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various

What is claimed is:

1. A device comprising:
   a filter holder, the filter holder comprising a tip portion;
   a nonwoven article disposed on an exterior surface of the tip portion of the filter holder; and
   an adaptor attached to the filter holder, the adaptor defining an aperture, wherein the adaptor is either attached to the filter holder in series and distal to the tip portion of the filter holder or attached to the filter holder in a Y-shaped configuration.

2. The device of claim 1, wherein the adaptor further comprises at least one rib formed on an interior surface of the adaptor.

3. The device of claim 1, wherein the filter holder and the adaptor are attached in series.

4. The device of claim 1, wherein the device comprises a Y-shaped configuration, and the device further comprises a housing configured to accept the Y-shaped configuration, wherein the housing comprises a waste collection container and a vent.

5. The device of claim 1, wherein the nonwoven article is configured to have a tube shape.

6. The device of claim 1, further comprising a cuvette, wherein the tip portion of the filter holder is configured to be inserted into the cuvette.

7. The device of claim 1, wherein the filter holder further comprises a sleeve disposed in the filter holder.

8. The device of claim 1, wherein the nonwoven article comprises a fibrous porous matrix and a plurality of concentration agent particles enmeshed in the fibrous porous matrix.

9. The device of claim 1, further comprising a pressure differential source comprising a syringe, a pump, or an aspirator.

10. The device of claim 1, further comprising a handle configured to be inserted in the filter holder, the handle comprising a feature or mark disposed at a distance from an end of the handle.

11. The device of claim 1, further comprising a resilient member disposed around at least a portion of an exterior surface of the nonwoven article.

* * * * *